(12) United States Patent
Horio

(10) Patent No.: US 9,739,854 B2
(45) Date of Patent: Aug. 22, 2017

(54) MAGNETIC RESONANCE IMAGING APPARATUS AND OUTPUT PATTERN DETERMINING METHOD

(71) Applicant: HITACHI, LTD., Tokyo (JP)

(72) Inventor: Hideyuki Horio, Tokyo (JP)

(73) Assignee: HITACHI, LTD., Tokyo (JP)

( * ) Notice: Subject to any disclaimer, the term of this patent is extended or adjusted under 35 U.S.C. 154(b) by 428 days.

(21) Appl. No.: 14/381,788

(22) PCT Filed: Mar. 8, 2013

(86) PCT No.: PCT/JP2013/056444
§ 371 (c)(1),
(2) Date: Aug. 28, 2014

(87) PCT Pub. No.: WO2013/141043
PCT Pub. Date: Sep. 26, 2013

(65) Prior Publication Data
US 2015/0042341 A1    Feb. 12, 2015

(30) Foreign Application Priority Data

Mar. 21, 2012    (JP) .................................. 2012-063145

(51) Int. Cl.
*G01V 3/00* (2006.01)
*G01R 33/36* (2006.01)
(Continued)

(52) U.S. Cl.
CPC .......... *G01R 33/3621* (2013.01); *A61B 5/055* (2013.01); *G01R 33/3415* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| 7,026,818 B2 | 4/2006 | Machida et al. |
| 7,157,910 B2 | 1/2007 | Van Den Brink |
| (Continued) | | |

FOREIGN PATENT DOCUMENTS

| JP | 2003-334177 | 11/2003 |
| JP | 2005-529705 | 10/2005 |

OTHER PUBLICATIONS

Translation of JP 2003-334177 A listed in the IDS, publication date: Nov. 25, 2003.*
International Search Report in PCT/JP2013/056444.

*Primary Examiner* — Walter L Lindsay, Jr.
*Assistant Examiner* — Frederick Wenderoth
(74) *Attorney, Agent, or Firm* — Cooper & Dunham LLP

(57) ABSTRACT

In order to obtain high-quality images easily with high flexibility for imaging conditions and apparatus configuration changes in an MRI apparatus using a multi-element coil, an output pattern identifying a synthesizing mode of the respective reception signals received by the respective elements comprising a reception coil is determined according to imaging conditions in the present invention. The determination is performed so that, for example, at least one of a covering rate of an imaging range, an S/N ratio of the final image, and element utilization efficiency becomes the best. The output pattern is comprised of information identifying one or more elements that use reception signals and a synthetic pattern synthesizing the reception signals among the elements to be used. The synthetic pattern, for example, is selected in advance from among a plurality of synthetic pattern candidates to be stored according to a synthesizing method.

12 Claims, 17 Drawing Sheets

(51) Int. Cl.
*A61B 5/055* (2006.01)
*G01R 33/3415* (2006.01)
*G01R 33/385* (2006.01)
*G01R 33/56* (2006.01)

(52) U.S. Cl.
CPC ..... *G01R 33/3607* (2013.01); *G01R 33/3664* (2013.01); *G01R 33/385* (2013.01); *G01R 33/56* (2013.01)

(58) Field of Classification Search
USPC .......................................... 399/322; 324/322
See application file for complete search history.

(56) References Cited

U.S. PATENT DOCUMENTS

| | | | |
|---|---|---|---|
| 2002/0125888 A1* | 9/2002 | Visser | G01R 33/3415 324/318 |
| 2003/0132750 A1* | 7/2003 | Machida | G01R 33/3415 324/322 |
| 2006/0006867 A1 | 1/2006 | Van Den Brink | |
| 2006/0087320 A1 | 4/2006 | Machida et al. | |

* cited by examiner

FIG.2
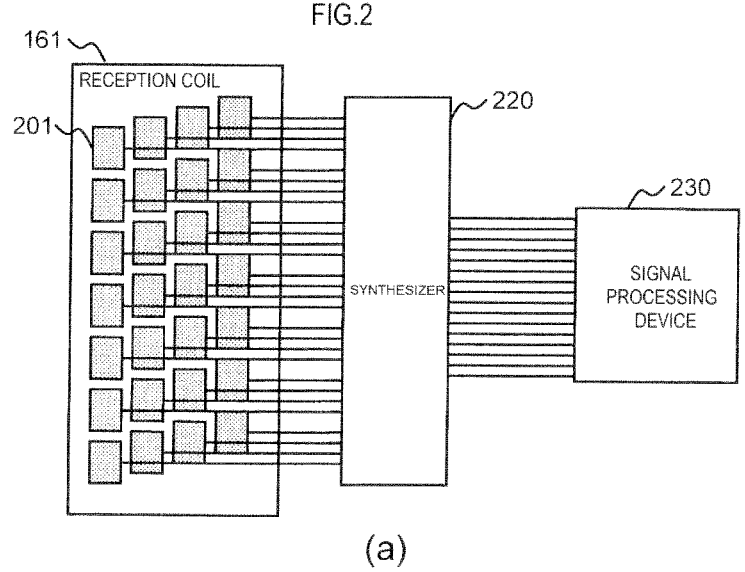
(a)
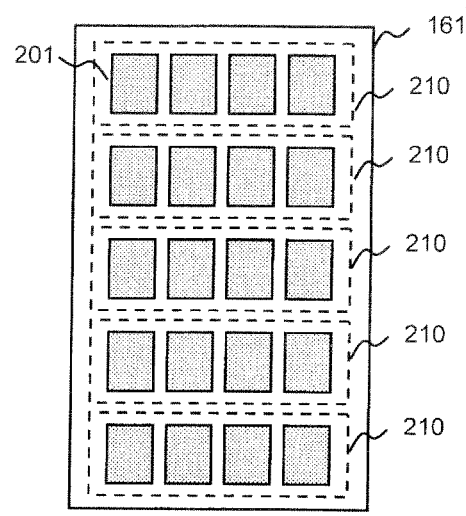
(b)

FIG.4

| SUB-COIL NAME ~321 | POSITION INFORMATION ~322 | SYNTHETIC PATTERN CANDIDATE NAME ~323 | SYNTHE- SIZING NUMBER ~324 | SYNTHETIC PATTERN CANDIDATE ~325 | OUTPUT CHANNEL NUMBER ~326 |
|---|---|---|---|---|---|
| #001 | | A | 1 | | 4 |
| | | B | 2 | | 2 |
| | | C | 3 | | 2 |
| | | D | 4 | | 1 |
| #002 | | A | 1 | | 5 |
| | | B | 2 | | 3 |
| | | C | 3 | | 2 |
| | | D | 4 | | 2 |
| | | E | 5 | | 1 |
| #003 | | | | | |

320

(a)

|  | #001 | #002 | #003 | #004 | #005 | #006 | #007 | REMAINDER |
|---|---|---|---|---|---|---|---|---|
| 16ch | 1 | 2 | 3 | 4 | 3 | 2 | 1 | 0 |
|  |  |  |  |  |  |  |  |  |
| 32ch | 1 | 2 | 3 | 4 | 3 | 2 | 1 | 16 |
|  | 1 | 2 | 3 | 8 | 3 | 2 | 1 | 12 |
|  | 1 | 2 | 8 | 8 | 8 | 2 | 1 | 2 |
|  | 1 | 3 | 8 | 8 | 8 | 3 | 1 | 0 |
| . |  |  |  |  |  |  |  |  |
| 8ch | 1 | 2 | 3 | 4 | 3 | 2 | 1 | -8 |
|  | 1 | 1 | 2 | 3 | 2 | 1 | 1 | -3 |
|  | 1 | 1 | 1 | 2 | 1 | 1 | 1 | 0 |

| SUB-COIL NAME ~321 | POSITION INFORMATION ~322 | SYNTHETIC PATTERN CANDIDATE NAME ~323 | SYNTHESIZING NUMBER ~324 | SYNTHETIC PATTERN CANDIDATE ~325 | OUTPUT CHANNEL NUMBER ~326 |
|---|---|---|---|---|---|
| #001 | | A | 1 | | 4 |
| | | B | 2 | | 2 |
| | | C | 2 | | 3 |
| | | D | 2 | | 3 |
| | | E | 2 | | 3 |
| | | F | 3 | | 2 |
| | | G | 3 | | 2 |
| | | H | 4 | | 1 |

320

FIG.17
| SUB-COIL NAME 321 | POSITION INFORMATION 322 | SYNTHETIC PATTERN CANDIDATE NAME 323 | SYNTHESIZING NUMBER ROW/COLUMN 324 | SYNTHETIC PATTERN CANDIDATE 325 | OUTPUT CHANNEL NUMBER 326 |
|---|---|---|---|---|---|
| #001 | | A | 1<br>1/1 |  | 4 |
| | | B | 2<br>2/1 |  | 2 |
| | | C | 4<br>4/1 |  | 1 |
| #002 | | A | 1<br>1/1 |  | 8 |
| | | B | 2<br>2/1 | 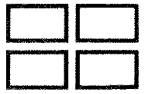 | 4 |
| | | C | 2<br>1/2 |  | 4 |
| | | D | 4<br>2/2 |  | 2 |
| | | E | 8<br>4/4 |  | 1 |

MAGNETIC RESONANCE IMAGING APPARATUS AND OUTPUT PATTERN DETERMINING METHOD

TECHNICAL FIELD

The present invention relates to a nuclear magnetic resonance imaging (hereinafter, referred to as "MRI") technique that measures a nuclear magnetic resonance (hereinafter, referred to as "NMR") signal from hydrogen, phosphorus, etc. in an object to create images of nuclear density distribution, relaxation time distribution, etc., in particular, to techniques for automatically selecting a receiving element to receive an NMR signal and synthesizing reception signals.

BACKGROUND ART

An MRI apparatus measures an NMR signal generated by atomic nucleus spin that comprises tissue of an object in particular to a human body and creates images of shapes and functions of human head, abdomen, four limbs, etc, two-dimensionally or three-dimensionally. During imaging, phase encoding that varies depending on the gradient magnetic field is given to an NMR signal, and frequency encoding is performed for the NMR signal, and it is measured as time-series data. The measured NMR signal is reconstructed to an image by performing a two-dimensional or three-dimensional Fourier transform.

Reception coils that receive an NMR signal has a multi-element coil that includes multiple elements. An MRI apparatus to which a multi-element coil can be connected determines elements to be used for measuring in the light of a disposed position, an imaging range, a signal strength, etc. of the respective elements (for example, see PTL 1 and PTL 2).

By the way, because an NMR signal to be received (reception signal) is an analog signal, A/D conversion needs to be performed. When the number of A/D converters (channels) is equal to or less than the number of elements comprising the multi-element coil, reception signals received by the respective elements are arbitrarily reduced to equal to or less than the number of channels by synthesizing the signals using a synthesizer and are output to the respective A/D converters.

In this case, if the elements that synthesize the reception signals are fixed, this cannot be addressed flexibly according to changes of imaging conditions, in particular an imaging range. Also, it takes much time and efforts for a user to change a synthetic form according to the imaging conditions, and, in addition, it is also difficult to keep quality of images to be output.

In order to solve these problems, for example, a method that maintains an index to determine image quality by associating reception signals with all the synthesizable combinations in advance and determines a combination of the reception signals to be synthesized according to an imaging range and desirable image quality is provided (for example, see PTL 3).

CITATION LIST

Patent Literature

PTL 1: Japanese Unexamined Patent Application Publication No. 2006-528509
PTL 2: Japanese Unexamined Patent Application Publication No. 2006-175058
PTL 3: Japanese Unexamined Patent Application Publication No. 2011-36452

SUMMARY OF INVENTION

Technical Problem

However, the technique of the above PTL 3, for example, needs to newly create database again when a configuration change of the reception coils where a new element is added or where an element is reduced is caused, which cannot deal with the configuration change easily.

The present invention is made in consideration of the above problems and is an MRI apparatus that uses a multi-element coil. The present invention is highly flexible for changes of imaging conditions and apparatus configuration of an apparatus in which the number of channels is less than the number of elements and is aimed at providing a technique to obtain high quality images easily.

Solution to Problem

The present invention is an MRI apparatus that uses a multi-element coil and automatically determines an output pattern that identifies a synthetic form of the respective reception signals received by the respective elements comprising a reception coil according to imaging conditions for an apparatus in which the number of channels is less than the number of elements. The determination is performed so that at least one of a covering rate of imaging range, an S/N ratio of the final image, and element utilization efficiency is the best, for example. The output pattern is comprised of information to identify one or more elements that uses reception signals and a synthetic pattern to synthesize reception signals among elements to be used. A synthetic pattern is selected in advance from among a plurality of synthetic pattern candidates to be held according to a synthesizing method, for example.

Advantageous Effects of Invention

The present invention, an MRI apparatus that uses a multi-element coil, is highly flexible for changes of imaging conditions and apparatus configuration of an apparatus in which the number of channels is less than the number of elements and can obtain high quality images easily.

BRIEF DESCRIPTION OF DRAWINGS

FIG. 2(a) is a block diagram of a reception system of the first embodiment, and FIG. 2(b) is an explanatory diagram to describe a reception coil.

FIG. 4 is an explanatory diagram to describe a synthetic pattern table of the first embodiment.

FIG. 11 is an explanatory diagram to describe a synthetic pattern table of a transformation example of the second embodiment.

FIG. 17 is an explanatory diagram to describe a synthetic pattern table of the forth embodiment.

DESCRIPTION OF EMBODIMENTS

First Embodiment

Hereinafter, the first embodiment adopting the present invention will be described with diagrams. Also, in all the diagrams to describe the respective embodiments, the repeated explanations will be omitted for the same functions with the same name and the same code.

Figure 1:
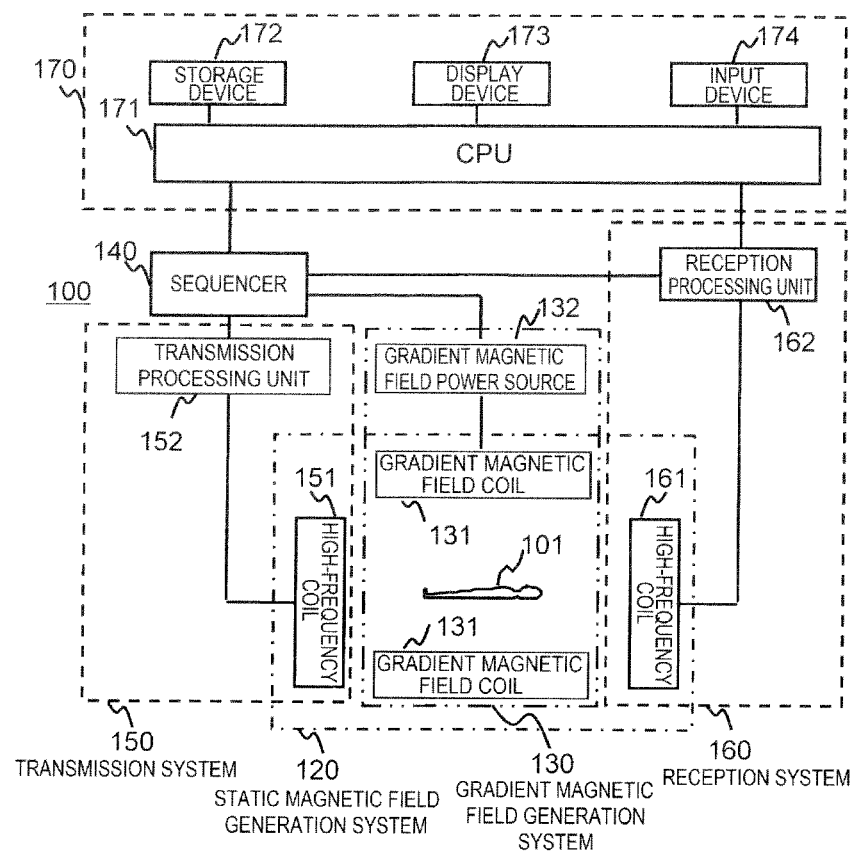
FIG. 1 is a block diagram showing an overall configuration of an MRI apparatus of the first embodiment.

First, the entire overview of an example of an MRI apparatus in the present embodiment will be described. FIG. 1 is a block diagram showing an overall configuration of the MRI apparatus 100 of the present embodiment. The MRI apparatus 100 of the present embodiment obtains tomographic images of an object using the NMR phenomenon and includes the static magnetic field generation system 120, the gradient magnetic field generation system 130, the transmission system 150, the reception system 160, the control system 170, and the sequencer 140 as shown in FIG. 1.

The static magnetic field generation system 120 generates homogeneous static magnetic field in a direction orthogonal to the body axis in a space around the object 101 in the case of the vertical magnetic field method as well as in a body-axis direction in the case of the horizontal magnetic field method and includes a static magnetic field generation source of the permanent magnet method, the normal conduction method, or the super conduction method that is disposed around the object 101.

The gradient magnetic field generation system 130 includes the gradient magnetic field coil 131 wound in the three axis directions X, Y, and Z that are the coordinate systems (apparatus coordinate systems) of the MRI apparatus 100 as well as the gradient magnetic field power source 132 to drive the respective gradient magnetic field coils and drives the gradient magnetic field power source 132 of the respective gradient magnetic field coils 131 according to a command from the sequencer 140 to be described later to apply the gradient magnetic fields Gx, Gy, and Gz in the three axis directions X, Y, and Z.

The transmission system 150 irradiates a high-frequency magnetic field pulse (hereinafter, referred to as "RF pulse") to the object 101 in order to cause nuclear magnetic resonance to an atomic nucleus spin of an atom comprising the body tissue of the object 101 and includes the transmission processing unit 152 having a high-frequency oscillator (synthesizer), modulator, and high-frequency amplifier as well as the high-frequency coil (transmission coil) 151 on the transmitting side. The high-frequency amplifier generates an RF pulse and outputs at a timing commanded from the sequencer 140.

The modulator amplifies and modulates an output RF pulse, the high-frequency amplifier amplifies the amplified and modulated RF pulse and provides it to the transmission coil 151 disposed in the vicinity of the object 101. The transmission coil 151 irradiates the provided RF pulse to the object 101.

The reception system 160 detects a nuclear magnetic resonance signal (echo signal, NMR signal) released by nuclear magnetic resonance of atomic nucleus spin comprising the body tissue of the object 101 and includes the high-frequency coil (reception coil) 161 on the receiving side and the reception processing unit 162 having a synthesizer, amplifier, orthogonal phase detector and A/D converter.

In the present embodiment, the reception coil 161 is to be a multi-element coil having a plurality of elements. The reception coil 161 is disposed in the vicinity of the object 101 and detects an NMR signal (reception signal) responded by the object 101 induced by an electromagnetic wave irradiated from the transmission coil 151 using the respective element. The reception signal is synthesized by the synthesizer, is amplified by the amplifier, and is divided into orthogonal two-system signals by the orthogonal phase detector at a timing commanded from the sequencer 140, and the respective signals are converted into digital quantity by the A/D converter and are transmitted to the control system 170. The details of the reception system 160 will be described later.

The sequencer 140 repeatedly applies an RF pulse and gradient magnetic field pulse according to the predetermined pulse sequence. Also, the pulse sequence is described about a high-frequency magnetic field, a gradient magnetic field, and a timing and strength of signal reception and is retained in the control system 170 in advance. The sequencer 140 operates according to a command from the control system 170 and transmits various commands required to correct data of tomographic images of the object 101 to the transmission system 150, the gradient magnetic field generation system 130, and the reception system 160.

The control system 170 performs various calculations such as overall operation control of the MRI apparatus 100, signal processing, and image reconstruction, displays the processing results, saves them, etc. as well as includes the CPU 171, the storage device 172, the display device 173, and the input device 174.

The storage device 172 is comprised of an internal storage device such as a hard disk and an external storage device such as an external hard disk, optical disk, and magnetic disk.

The display device 173 is a display device of CRT, liquid crystal, etc. The input device 174 is an interface to input various control information of the MRI apparatus 100 and control information processed by the control system 170, for example, and includes a trackball or a mouse and a keyboard.

The input device 174 is disposed in the vicinity of the display device 173. An operator checks the display device 173 and interactively inputs commands and data required for various processes of the MRI apparatus 100 through the input device 174.

The control system 170 of the present embodiment also performs signal synthetic embodiment control by a synthesizer in overall operation control of the MRI apparatus 100. The details of the present control will be described later.

According to the command input by an operator, the CPU 171 performs a program held in the storage device 172 in advance to achieve the respective processes of the control system 170 such as operation control of the MRI apparatus 100 and various data processes. For example, when data from the reception system 160 is input to the control system 170, the CPU 171 performs processes such as signal processing and image reconstruction and displays the consequent tomographic image of the object 101 on the display device 173 as well as stores it in the storage device 172.

In a static magnetic field space of the static magnetic field generation system 120 in which the object 101 is inserted, the transmission coil 151 and the gradient magnetic field coil 131 are installed so that they face the object 101 in the case of the vertical magnetic field method and so that they surround the object 101 in the case of the horizontal magnetic field method. Also, the reception coil 161 is installed so that it faces or surrounds the object 101.

Currently, the imaging target nuclide of an MRI apparatus that is clinically prevalent is a hydrogen nucleus (proton) that is the main component of the object 101. In the MRI apparatus 100, information relating to the space distribution of proton density or the space distribution of a relaxation time of an excited state is imaged, whereby the shapes or functions of human head, abdomen, four limbs, etc. are imaged in a two-dimensionally or three-dimensionally.

Next, the section related to synthesization of signals received by the respective elements of the reception system 160 of the present embodiment will be described. FIG. 2 is a diagram to describe the reception system 160 of the present embodiment, FIG. 2(a) is a diagram to describe the details of the reception system 160 of the present embodiment, and FIG. 2(b) is a diagram to describe the details of the reception coil 161 of the present embodiment.

As shown in the FIG. 2(a), the reception system 160 of the present embodiment includes the reception coil 161, the synthesizer 220, and the signal processing device 230.

The reception coil 161 is comprised of a plurality of the elements 201 that receives NMR signals respectively. The number of the elements 201 that the reception coil 161 includes is N (N is an integer of 2 or more). In the present figure, a case where N=28 is shown as an example. The configuration of the reception coil 161 is not limited to this case. There are no problems if a plurality of the elements 201 are included.

The signal processing device 230 amplifies, detects, and then performs A/D conversion for NMR signals (reception signals) received by the reception coil 161. The number M of channels (M is an integer of 1 or more) processable for the signal processing device 230 of the present embodiment is equal to or less than the number of the elements 201N. Hereinafter, channels processable for the signal processing device 230 are referred to as "reception channels". Also, in the present figure, a case where M=16 is shown as an example.

The synthesizer 220 synthesizes reception signals received by the respective elements 201 of the reception coil 161 according to a predetermined output pattern and converts the signals into output signals with the number M equal to or less than the reception channels to output the signals to the signal processing device 230.

The output pattern includes information identifying using elements where the reception signals are used as output signals and synthetic patterns identifying a mode to synthesize the reception signals among the using elements. The output pattern is created by the control system 170. The details of the output pattern will be described later. The synthesizer 220 can change a synthetic mode according to a control signal by software, synthesizes the reception signals input from the respective elements 201 according to a command from the control system 170, and then outputs the signals to the signal processing device 230.

Also, in the present embodiment, only the reception signals among the elements 201 arranged in a specific direction are synthesized. Hereinafter, the arrangement direction of the elements 201 that synthesizes the respective reception signals is referred to as "synthetic direction". For example, as shown in FIG. 2(b), in the reception coil 161 where the four elements 201 in the lateral (row) direction and the five elements 201 in the longitudinal (column) direction are disposed in array, the arrangement direction of pairs of the elements 201 that synthesizes the reception signals is only the lateral (row) direction or only the longitudinal (column) direction. Also, the coil shown in FIG. 2(b) is disposed at the top and bottom of the object 101, and the synthetic direction may be vertical in a case such as when one of the reception coil 161 is configured.

Hereinafter, in the present embodiment, a case where a synthetic direction is only the lateral (row) direction will be described as an example. Also, in order to make the description easier, a group of the elements 201 that is possible to synthesize the reception signals, i.e., a group of the elements 201 arranged in the synthetic direction is referred to as "sub-coil 210".

Also, in FIG. 2(b), although a case where a plurality of the elements 201 are arranged in array in the lateral (row) direction and the longitudinal (column) direction respectively by a certain number is shown as an example, the arrangement of the elements 201 is not limited to this case. For example, the number of the elements may vary depending on the synthetic direction (in this case, the lateral (row) direction).

Figure 3:
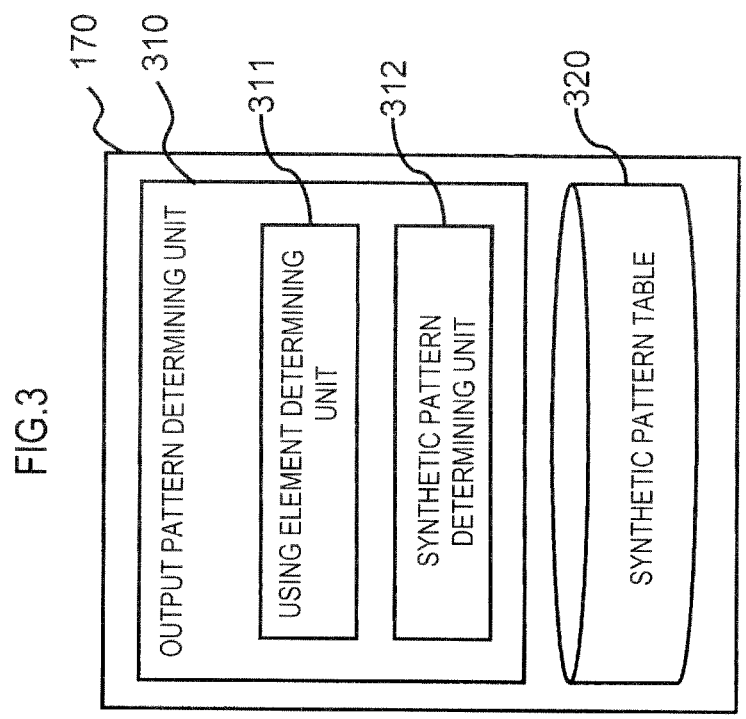
FIG. 3 is a functional block diagram of a control system of the first embodiment.

Next, generation processing of the above output pattern in the control system 170 will be described. In order to generate the output pattern, the control system 170 includes the output pattern determining unit 310 and the synthetic pattern table 320 as shown in FIG. 3. The output pattern determining unit 310 achieves a program stored in the storage device 172 in advance by the CPU 171 loading the program into a memory and executing it. Also, the synthetic pattern table 320 is constructed on the storage device 172.

Information related to an imaging range and a selectable synthetic pattern for the respective sub-coils 210 is registered in the synthetic pattern table 320. A synthetic pattern is a synthetic mode of elements that synthesizes reception signals. An example of the synthetic pattern table 320 is shown in FIG. 4. As shown in the present figure, the information (sub-coil name) 321 that identifies the respective sub-coils 210 for the respective sub-coils 210, the position information 322 that can identify region information which the respective sub-coils 210 can cover, and information about a synthetic pattern are registered in the synthetic pattern table 320. As the information about a synthetic pattern, the synthetic pattern candidate 325, the information (synthetic pattern candidate name) 323 that identifies the respective synthetic pattern candidates, the maximum number (synthesizing number) 324 of reception signals to be synthesized for the synthetic pattern candidate, and the channel (output channel) number 326 to be output from the synthesizer 220 when reception signals are synthesized according to the synthetic pattern candidate are registered.

As the position information 322, for example, the relative positions of the respective sub-coils 210 are registered for the standard position of the sub-coil 210. In this case, when the reception coil 161 is installed in the MRI apparatus 100, a position of the standard sub-coil 210 in a device coordinate system that the MRI apparatus 100 has is determined. Then, positions in the device coordinate system for the other sub-coils 210 are determined respectively.

If the reception coil 161 is pre-installed in the MRI apparatus 100, positions of the respective sub-coils in a device coordinate system may be stored as the position information 322.

Also, the synthetic pattern candidate 325 where each synthesizing number 324 is 1 is registered in the present embodiment.

For a case where the synthesizing number 324 is 1, when there are a plurality of synthetic pattern candidates, one of a synthetic pattern candidate is selected in advance and registered. Also, in FIG. 4, a case where the sub-coil 210 with the sub-coil name #001 includes the four elements 201 as well as the sub-coil 210 with the sub-coil name #002 includes the five elements 201 is shown as an example.

The output pattern determining unit 310 includes the using element determining unit 311 and the synthetic pattern determining unit 312. The using element determining unit 311 determines the elements 201 that uses the reception signals by the element 201 group in the synthetic direction, i.e., by the sub-coil 210. Also, the synthetic pattern determining unit 312 determines synthetic patterns in the respective using sub-coils 210. Then, the output pattern determining unit 310 determines an output pattern using the determined using elements 201 and the synthetic patterns and provides a command so as to synthesize the reception signals according to the determined output pattern to the synthesizer 220.

The using element determining unit 311 identifies the smallest sub-coil 210 covering an imaging range that meets imaging conditions set by a user and specifies the sub-coil as the using sub-coil 210. The using sub-coil is a sub-coil that uses the reception signals to form output signals in the synthesizer 220. The identification is performed based on the position information 322 of the synthetic pattern table 320. Then, the elements 201 included in the using sub-coil 210 are specified as the using elements 201.

The synthetic pattern determining unit 312 determines a synthetic pattern of the using elements 201 by the sub-coil 210. At this time, the synthetic pattern of the respective using sub-coils 210 is determined so that the total number of output channels by the respective using sub-coils 210 is the maximum value equal to or less than the number of the reception channels. For the respective using sub-coils 210, the synthetic pattern is selected and determined from among the synthetic pattern candidates 325 registered in the synthetic pattern table 320.

At this time, in the present embodiment, the maximum number (synthesizing number) 324 to synthesize reception signals is the same for the respective using sub-coils 210. In this restriction, within a range where the total of the output channel number 326 of the respective using sub-coils 210 does not exceed the number M of the reception channels, the synthetic pattern candidates 325 with the minimum synthesizing number 324 is selected, and then the synthetic pattern of the respective using sub-coils 210 is determined.

For example, as shown in FIG. 4, there are the three using sub-coils 210 of #001, #002, and #003 where the number of the elements 201 same as #001 is four. At this time, if the minimum synthesizing number 1 is selected when the number M of the reception channels is 8, the total number of output channels is 13. If the next minimum synthesizing number 2 is selected, the total number of output channels is 7. Therefore, the synthetic pattern candidates 325 of the synthesizing number 2 are selected respectively. That is, the synthetic pattern candidate B is selected for #001, #002, and #003.

Figure 5:
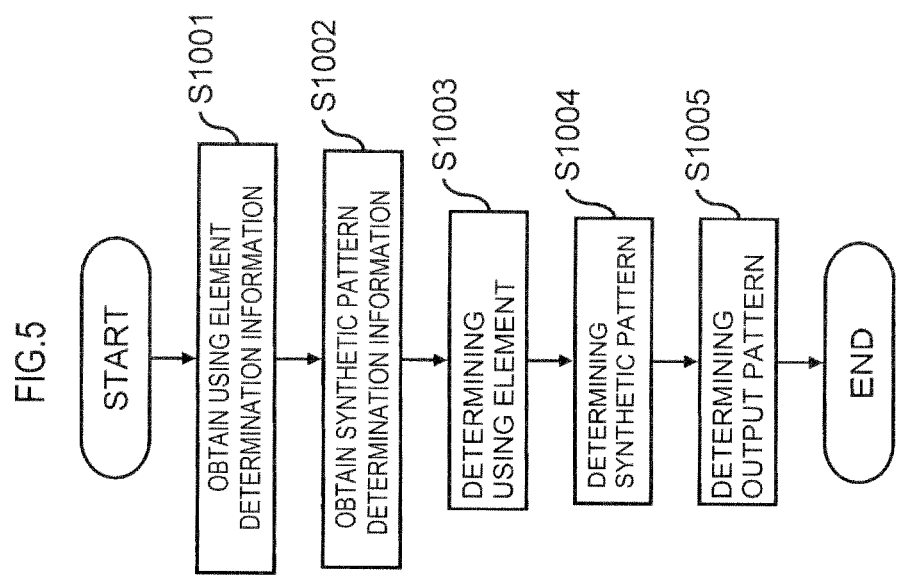
FIG. 5 is a flow chart for determining an output pattern of the first embodiment.

The process flow of output pattern determination by the output pattern determining unit 310 of the present embodiment will be described referring to a specific example. FIG. 5 is the process flow of output pattern determination of the present embodiment. Also, FIGS. 6(*a*) to (*c*) are diagrams to describe the present process. Also, the output pattern determining unit 310 of the present embodiment starts the process immediately after a user sets imaging conditions and receives a command to start imaging.

Figure 6:
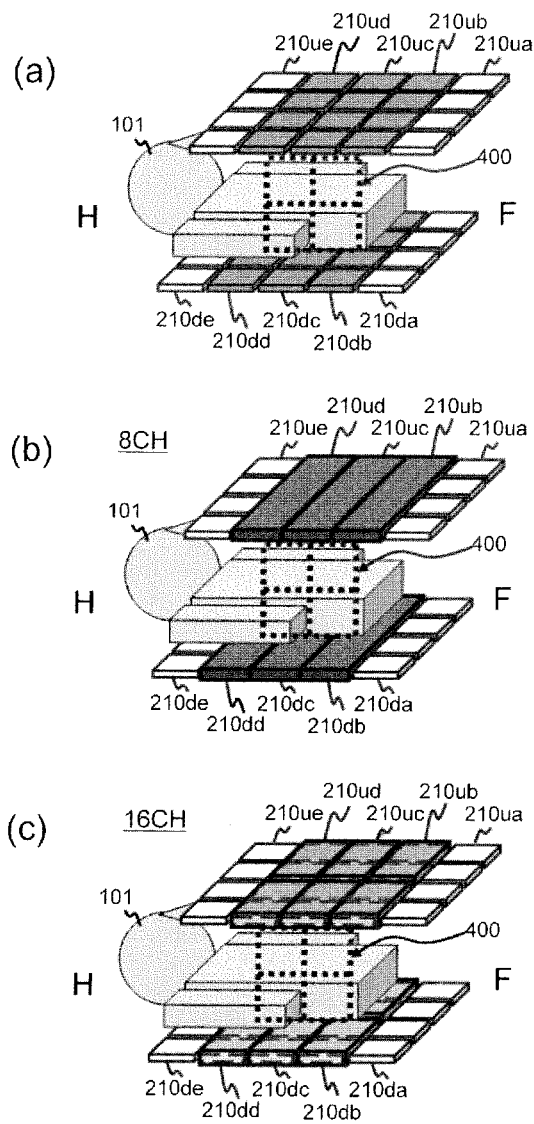
FIGS. 6(a) to 6(c) are explanatory diagrams to describe the output pattern determination process of the first embodiment.

In FIGS. 6(*a*) to (*c*), a case where the number of elements N of the reception coil 161 is 40 is shown as an example. In this section, the respective elements 201 are respectively disposed in an array of 4 columns by 5 rows in the position where the elements face each other between the top and bottom of the object 101. A synthetic direction of the elements 201 is the row direction. Therefore, the sub-coil 210 is comprised of the four elements 201 in the same row. Information related to a synthetic pattern that the respective sub-coils 210 can select and that is to be registered in the synthetic pattern table 320 is the same as that of #001 in FIG. 4.

Also, in FIGS. 6(*a*) to (*c*), the ten sub-coils 210 are the sub-coils 210*ua*, 210*ub*, 210*uc*, 210*ud*, 210*ue*, 210*da*, 210*db*, 210*dc*, 210*dd*, and 210*de* respectively.

The output pattern determining unit 310 obtains information (using element determination information) to determine the using sub-coil 210 and the using element 201 (Step S1001). At this time, information relating to an imaging range is obtained from the imaging conditions, and the position information 322 of the respective sub-coils 210 is obtained from the synthetic pattern table 320.

Next, the output pattern determining unit 310 obtains information (synthetic pattern determination information) to determine a synthetic pattern (Step S1002). At this time, the number M of the reception channels of the signal processing device 230 is obtained. The number M of the reception channels of the signal processing device 230 is stored as device information in the storage device 172 in advance. Also, Either Step S1001 or Step S1002 may be performed first.

Next, the using element determining unit 311 determines the using sub-coil 210 and the using element 201 based on the information obtained in Step 1001 (Step S1003).

As described above, the using element determining unit 311 determines the smallest sub-coil 210 that covers an imaging range as the using sub-coil 210. At this time, as shown in FIG. 6(*a*), the six sub-coils 210 of 210*ub*, 210*uc*, 210*ud*, 210*db*, 210*dc*, and 210*dd* that cover the imaging range 400 are selected as the using sub-coils 210. Then, the elements 201 of the using sub-coils 210 are determined as the using elements 201.

Next, the synthetic pattern determining unit 312 determines a synthetic pattern of the respective using subcoils 210 using the number of the reception channels obtained in Step S1002, the synthesizing number 324 of the determined using subcoils 210, and the output channel number 326 (Step S1004).

For example, when the number M of the reception channels of the signal processing device 230 is 8 if the synthesizing number of the respective using subcoils 210 is 1, the total output channel number is 24, and resulting in an inappropriate number. Next, if the synthesizing number is 2, the total output channel number is 12, and resulting in an inappropriate number similarly. Next, a case where the synthesizing number is 3 is also similar. Next, if the synthesizing number is 4, the total output channel number is 6, and resulting in an appropriate number. Therefore, the synthetic pattern determining unit 312 selects the synthetic pattern candidate D whose synthesizing number 324 is 4 as a synthetic pattern of the respective using subcoils 210 when the number M of the reception channels is 8. At this time, as shown in FIG. 6(b), the reception signals from the six sub-coils 210 of 210ub, 210uc, 210ud, 210db, 210dc, and 210dd are synthesized in the synthetic pattern candidate D.

For example, when the number M of the reception channels of the signal processing device 230 is 16 if the synthesizing number of the respective using subcoils 210 is 1, the total output channel number is 24, and resulting in an inappropriate number. Next, if the synthesizing number is 2, the total output channel number is 12, and resulting in an appropriate number. Therefore, the synthetic pattern determining unit 312 selects the synthetic pattern candidate B as a synthetic pattern of the respective using subcoils 210 when the number M of the reception channels is 16. At this time, as shown in FIG. 6(c), the reception signals from the six sub-coils 210 of 210ub, 210uc, 210ud, 210db, 210dc, and 210dd are synthesized in the synthetic pattern candidate B.

Then, the output pattern determining unit 310 determines an output pattern using information of the using sub-coils 210 and the synthetic pattern (Step S1005), and then ends the processes. Here, the output pattern determining unit 310 does not use reception signals from the sub-coils 210 (in this case, the sub-coils 210ua, 210ue, 210da, and 210de) other than the using sub-coils 210 and determines an output pattern so that the reception signals from the using sub-coils 210 are synthesized using the synthetic pattern determined in the above Step S1004.

Figure 7:
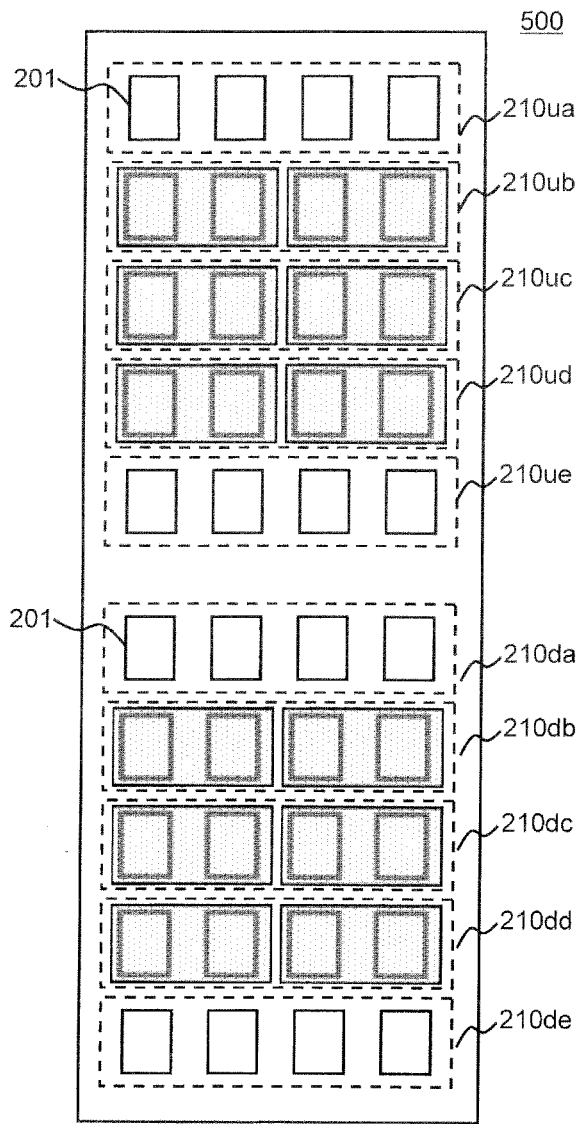
FIG. 7 is an explanatory diagram to describe the output patterns of the first embodiment.

For example, an image of the output pattern 500 created when the number M of reception channels is 16 in the FIG. 6(c) case is shown in FIG. 7. Here, in order to make the description easier, the sub-coils 210ua, 210ub, 210uc, 210ud, and 210ue are shown in the upper half, and the sub-coils 210da, 210db, 210dc, 210dd, and 210de are shown in the lower half. The output pattern 500 synthesizes the respective reception signals of the two right-side elements 201 and the two left-side elements 201 in the diagram for the respective sub-coils 210ub, 210uc, 210ud, 210db, 210dc, and 210dd into output signals. The synthesizer 220 generates output signals by synthesizing the reception signals input from the respective elements 201 according to the output pattern and outputs the output signals to the signal processing device 230.

Also, the output pattern determining unit 310 may display a determined output pattern on the display device 173. For example, as shown in FIG. 7, the display of combinations for which the elements 201 are synthesized may be superimposed on the layout of the respective elements 201.

Then, the control system 170 of the present embodiment provides a command to the synthesizer 220 to synthesize reception signals according to an output pattern when the output pattern determining unit 310 determines an output pattern, controls operations of the respective parts, and then starts imaging.

As described above, a magnetic resonance imaging apparatus of the present embodiment includes the reception coil 161 having a plurality of the elements 201, one or more reception channels, information identifying the using elements 201 to be used for forming output channels from among the multiple elements, the output pattern determining unit 310 determining a synthetic pattern for synthesizing reception signals of the using elements 201 as an output pattern so that the number of the output channels that forms the synthetic pattern is equal to or less than the number of the reception channels, and the synthesizer 220 that synthesizes the reception signals received by the using elements 201 according to output pattern into the output channels and outputs the signals to the reception channels.

Also, the output pattern determining unit 310 may determine the output pattern so that an imaging range specified by the imaging conditions is included.

Also, a plurality of the elements 201 comprise the sub-coil 210 for each predetermined number, and the output pattern determining unit 310 may include the imaging range 322 for the respective sub-coils 210, the synthetic pattern candidates 325 that can be obtained by the elements 201 comprising the sub-coil 210, the synthetic pattern table 320 keeping the output channel number 326 that is formed in the sub-coil 210 which is a candidate of the respective synthetic patterns, the using element determining unit 311 determining the using elements 201 in a unit of the sub-coil 210 according to an imaging range of the imaging conditions and determining the sub-coil 210 including the using elements 201 as the using sub-coil 210, and the synthetic pattern determining unit 312 determining the synthetic pattern for the respective using sub-coils 210 so that the total number of the output channels by the respective using sub-coils 210 is a maximum value equal to or less than the number of the reception channels.

Also, the synthetic pattern table 320 further keeps the synthesizing number 324 that is a maximum reception channel number synthesized by the synthetic pattern candidates 325 for the respective synthetic pattern candidates 325, and the synthetic pattern determining unit 312 may determine the synthetic pattern candidates 325 with the same synthesizing number 324 as a synthetic pattern for the respective using sub-coils 210.

Also, the using elements that synthesize the reception signals may be arranged in one direction.

Also, a magnetic imaging apparatus of the present embodiment comprising: a reception coil that includes a plurality of sub-coils of one or more elements; one or more reception channels equal to or less than the number of the elements; a synthesizer that synthesizes reception signals received by the respective elements into the reception channels according to a predetermined output pattern; and a synthetic pattern table keeping the number of output channels that the sub-coil forms in an imaging range for the respective sub-coils, a synthetic pattern candidate of the reception signal that can be obtained by the elements that comprise the sub-coil, and the respective synthetic pattern candidates, wherein a determining method of the output pattern may include a using sub-coil determining unit determining a sub-coil used to synthesizing the reception signals as a using sub-coil according to an imaging range of the imaging conditions, a synthetic pattern determining unit determining a synthetic pattern from synthetic pattern candidates of the respective using sub-coils so that the total number of output channels of the using sub-coil is a maximum value equal to or less than the number of the reception channels, and an output pattern determining unit determining the output pattern from the using sub-coil and the synthetic pattern.

That is, according to the present embodiment, only reception signals from the elements 201 according to an imaging range specified by imaging conditions are used, and the reception signals are synthesized so that reception channels are used maximally. Synthesization is performed only for a predetermined synthetic direction of a plurality of the elements 201.

In the present embodiment, the synthetic pattern candidates 325 and the output channel number 326 are registered in the synthetic pattern table 320 in advance by the sub-coil 210 comprised of a group of the elements 201 for each synthetic direction for the respective synthesizing numbers 324. Then, the synthetic pattern candidates 325 whose maximum value of the synthesizing numbers 324 of reception signals in the respective using sub-coils 210 is the same and that can maximally use reception channels of the signal processing device 230 are determined as synthetic patterns for the respective using sub-coils 210. Then, an output pattern is determined from the synthetic patterns of the determined using elements 201 and is synthesized by the synthesizer 220.

Therefore, in the present embodiment, the optimal elements 201 are automatically determined according to an imaging range, and a synthetic pattern of reception signals among the elements 201 that uses reception channels maximally is determined automatically. Therefore, reception signals minimally required for generating an image in an imaging range in the synthesizer 220 for each imaging are synthesized in a mode where reception channels are maximally utilized and can be used to reconstruct and synthesize images. For this reason, according to the present embodiment, high quality images with a good S/N ratio can be obtained without a burden on a user.

Furthermore, a synthetic pattern to be used is selected from among the synthetic pattern candidates 325 registered in the synthetic pattern table 320 in advance for each group of the elements 201 (sub-coil 210) in the synthetic direction. Therefore, even in a case where the elements 201 is increased or decreased, only the relevant elements 201 of the synthetic pattern table 320 should be updated. The update of the synthetic pattern table 320 does not require special measurement, calculation, etc. for the update. Therefore, according to the present embodiment, when an output pattern that identifies a synthesizing mode for reception signals of the respective elements 201 is determined, the present embodiment can flexibly correspond to the increase or decrease of the elements 201.

Second Embodiment

Next, the second embodiment adopting the present invention will be described. In the present embodiment, while reception signals in an imaging range are being processed, synthesizing the reception signals is avoided for the elements 201 closer to an attention region in the imaging range, and the reception signals are turned into independent output signals.

As described above, in the case of the same imaging range, the more the number of channels to be used increases, the more the S/N ratio improves. Therefore, in the present embodiment, the elements 201 closer to an attention region in an imaging range select a synthetic pattern with the large number of channels. In the present embodiment, an attention region in an imaging range is the center of the imaging range.

The configuration of the MRI apparatus 100 of the present embodiment is basically similar to the first embodiment. However, because items that are prioritized when a synthetic pattern of the respective using sub-coils 210 is determined vary, the process of the synthetic pattern determining unit 312 varies. Hereinafter, focusing on different configurations from the first embodiment, the present embodiment will be described.

In the synthetic pattern determining unit 312 of the present embodiment, the using sub-coils 210 closer to the center of an imaging range (imaging center) specified by the imaging conditions select the synthetic pattern candidates 325 with the large output channel numbers 326 to determine a synthetic pattern to be sued for an output pattern. Selection is performed by referring the synthetic pattern table 320. Also, if a plurality of the synthetic pattern candidates 325 with the same output channel number 326, a synthetic pattern candidate 325 with the smallest synthesizing number 324 is determined as a synthetic pattern of the using sub-coil 210.

In order to determine output channel numbers of the respective using sub-coils 210, the output channel numbers are assigned to the respective using sub-coils 210 according to a distance from the imaging center. The distance is a distance between the imaging center and the centers of the respective using sub-coils 210. At this time, in the present embodiment, in order to cover an imaging range, at least one output channel must be assigned to all the using sub-coils 210.

Hereinafter, the method to assign output channel numbers to the respective using sub-coils 210 of the present embodiment according to a distance from the imaging center will be described using a specific example. Here, a case where the using sub-coils are seven (#001, #002, #003, #004, #005, #006, and #007) is described as an example. Also, the respective using sub-coils 210 include the eight elements 201 in a synthetic direction.

Figure 8:
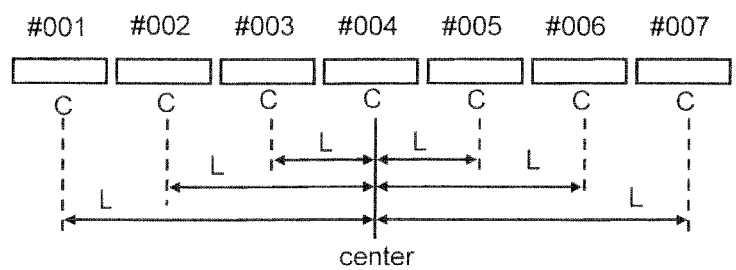
FIG. 8(a) is an explanatory diagram to describe a distance between the using sub-coils and the center of imaging of the second embodiment.
FIG. 8(b) is an explanatory diagram to describe processes to assign the number of output channels to the respective using sub-coils of the second embodiment.

FIG. 8(a) is an image diagram to describe distances between the respective using sub-coils 210 and the imaging center. The synthetic pattern determining unit 312 of the present embodiment first calculates the distance L from the imaging center (Center) of the center C of the respective using sub-coils 210 using the position information 322. Then, the smallest output channel number is assigned to the using sub-coil 210 with the largest distance L.

At this time, if the reception channel number has a remainder, output channel numbers to be assigned are increased in order from a sub-coil with the smaller distance L to an assignable maximum value. Oppositely, if the reception channel number is insufficient, the assigned number is decreased to 1 in order from the larger distance L.

Assigning output channel numbers to the respective using sub-coils 210 will be described using a specific example. Here, the imaging center (Center) is the center of the using sub-coil 210 (#004), the distance is further in the order of #003, #002, and #001. Also, #005, #006, and #007 are centered on the imaging center in the opposite direction with the same distance as #003, #002, and #001.

For example, when the reception channel number M is 16, in order from the larger to the smaller, the distance L is assigned by 1 increment starting from 1 Therefore, as shown in the "16ch" row in the table of FIG. 8(b), assigning 1 to #001, 2 to #002, 3 to #003, 4 to #004, 3 to #005, 2 to #006, and 1 to #007 is performed. In this case, the total output channel number is 16, the reception channel number is equal to or less than 16, and the remainder is also 0. Therefore, this assignment is adopted.

When the reception channel number M is 32, as shown in the first row of "32ch" in the table of FIG. 8(b), assigning 1 to #001, 2 to #002, 3 to #003, 4 to #004, 3 to #005, 2 to #006, and 1 to #007 is first performed similarly. Then, the total output channel number is 16, the reception channel number has a remainder of 16 channels. In this case, the remainder channels are assigned in order from a shorter distance L from the imaging center. Specifically, in order from the shorter distance L from the imaging center, output channel numbers are increased to an assignable maximum value. In short, as shown in the second row of "32ch", first, the maximum value 8 is assigned to #004 whose distance L is the shortest. Then, the total output channel number is 20, and the remainder is 12 channels.

Next, as shown in the third row of "32ch", the maximum value 8 is assigned to #003 and #005 whose distance L is the next shortest. Then, the total output channel number is 30, and the remainder is 2 channels. Finally, as shown in the fourth row of "32ch", the 2 channels are assigned to #002 and #007 whose distances are the next shortest by 1 channel, and this assignment is adopted.

When the reception channel number is 8, as shown in the first row of "8ch" in the table of FIG. 8(b), assigning 1 to #001, 2 to #002, 3 to #003, 4 to #004, 3 to #005, 2 to #006, and 1 to #007 is first performed similarly. Then, the total channel number is 16, the reception channel number is eight channels short.

At this time, the assigned number is decreased to 1 in order from the larger distance L. Therefore, as shown in the second row of "8ch", first, the assigned numbers of #002 and #007 are decreased to 1 respectively, and the assigned numbers of #003, #004, and #005 are decreased by 1 accordingly. Then, the total channel number is 11, and the reception channel number is still three channels short. Next, as shown in the third row of "8ch", the assigned numbers of #003 and #005 are also decreased to 1, and the assigned number of #004 is decreased by 1 accordingly. Then, the total channel number is 8, and this assignment is adopted.

Figure 9:
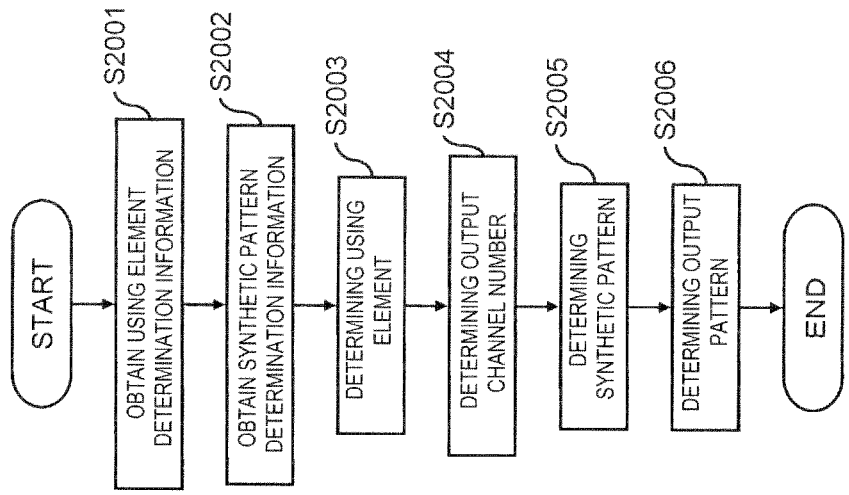
FIG. 9 is a process flow for determining an output pattern of the second embodiment.
Figure 10:
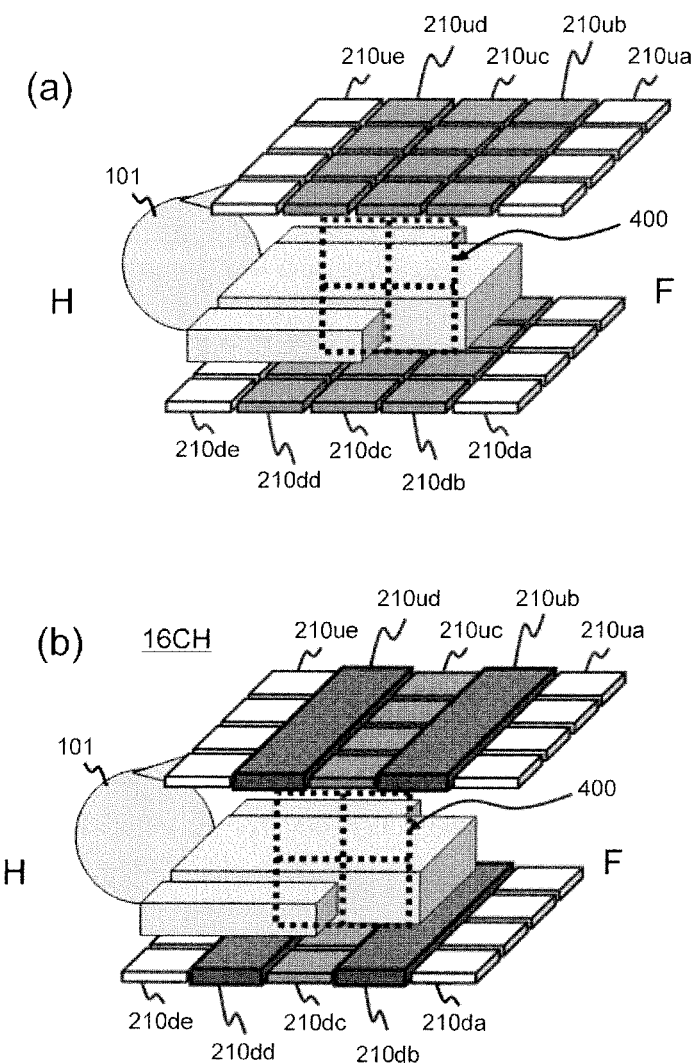
FIGS. 10(a) and 10(b) are explanatory diagrams to describe the output pattern determination process of the second embodiment.

Next, referring to a specific example, the output pattern determining process flow by the output pattern determining unit 310 of the present embodiment will be described. FIG. 9 is the process flow for the output pattern determining process of the present embodiment. Also, FIG. 10 is an explanatory diagram for the present process. Also, the output pattern determining unit 310 of the present embodiment starts the process immediately after a user completes the settings for imaging conditions and receives a command to start imaging. Also, the configuration of the reception coil 161 is similar to the reception coil 161 shown in FIG. 6(a) of the first embodiment.

The output pattern determining unit 310 obtains information to determine the using sub-coil 210 and the using elements 201 (Step S2001). Here, information related to an imaging range from imaging conditions as well as the position information 322 of the respective sub-coils 210 from the synthetic pattern table 320 are obtained. Also, in the present embodiment, the position information 322 is used for determining a synthetic pattern.

Next, the output pattern determining unit 310 obtains information to determine a synthetic pattern (Step S2002). Here, the reception channel number M of the signal processing device 230 is obtained. The reception channel number M of the signal processing device 230 stored in the storage device 172 as device information in advance. Also, even in the present embodiment, either Step S2001 or Step S2002 may be performed first.

Next, the using element determining unit 311 determines the using sub-coil 210 and the using elements 201 based on information obtained in Step S2001 (Step S2003).

Similarly to the first embodiment, the using element determining unit 311 determines the smallest sub-coil 210 that covers an imaging range as the using sub-coil 210. Here, as shown in FIG. 10(a), the six sub-coils 210 of 210ub, 210uc, 210ud, 210db, 210dc, and 210dd that cover the imaging range 400 are selected as the using sub-coils 210. The synthetic pattern determining unit 312

Next, the synthetic pattern determining unit 312 determines the output channel number of synthetic patterns of the respective using sub-coils 210 using the position information 322 obtained in Step S2001, the reception channel number M obtained in Step S2002, and the output channel number 326 of the determined using sub-coil 210 (Step S2004).

For example, the imaging center in an orthogonal direction centers on 210uc and 210dc. If the reception channel number M of the signal processing device 230 is 16, first, output channels are assigned one by one to 210ud, 210ub, 210dd, and 210db that are further from the imaging center. Then, the output channel number 2 increased by 1 is assigned to 210uc and 210dc. Then, the total output channel number is 8, and the remainder is 8 channels. The remainder of 8 channels is assigned to the using sub-coil 210 closest to the imaging center. Therefore, as shown in FIG. 10(b), the output channel numbers of 210ud, 210ub, 210dd, and 210db are 1 respectively, and those of 210uc and 210dc are 4 respectively.

Then, the synthetic pattern determining unit 312 refers to the synthetic pattern table 320 and determines the synthetic pattern candidate 325 with the smallest synthesizing number 324 from among the synthetic pattern candidates 325 having the output channel number 326 determined in Step S2004 as a synthetic pattern of the using sub-coil 210 (Step S2005).

Then, the output pattern determining unit 310 determines an output pattern using information of the using sub-coil 210 and the synthetic pattern (Step S2006), and then completes the process.

Also, the present embodiment may be configured so that a plurality of the synthetic pattern candidates 325 is registered in the synthetic pattern table 320 with the same synthesizing number 324. The synthetic pattern table 320 in this case is shown in FIG. 11. Here, only the sub-coil 210 (#001) in which the number of the elements 201 is 4 is shown. In this case, the synthetic pattern candidates 325 of the synthetic pattern table 320 include the layout of the respective elements 201 comprising the sub-coil 210 and information (element layout information) that can comprehend the elements 201 synthesizing the reception signals.

In this case, when the output channel number n assigned to the respective using sub-coils 210 is determined using the above method, the synthetic pattern determining unit 312 refers to the synthetic pattern table 320 in Step S2005, and then extracts the synthetic pattern candidate 325 whose output channel number 326 is n from among the using sub-coils 210. Then, the synthetic pattern candidate 325 with which the elements 201 further from the imaging center in a synthetic direction are synthesized is determined as a synthetic pattern of the using sub-coil 210.

Specifically, the synthetic pattern determining unit 312 calculates relative positions in a horizontal direction of the imaging center and the using sub-coil 210, and then selects the synthetic pattern candidate 325 with a smaller synthesizing number for the elements 201 in a position corresponding to the imaging center to determine the candidate as a synthetic pattern.

As described above, a magnetic resonance imaging apparatus of the present embodiment includes the reception coil 161 having a plurality of the elements 201, the synthesizer 220 that synthesizes one or more reception channels equal to or less than the number of the elements 201 and reception signals received by the respective elements 201 according to the predetermined output pattern to form an output channel equal to or less than the number of the reception channels and outputs to the reception channels, and the output pattern determining unit 310 that determines a synthetic pattern to synthesize information identifying the using elements 201 which is the one or more elements 201 to use the reception signals for forming the output channel according to imaging conditions and the reception signals among the using elements 201 as an output pattern.

Also, the output pattern determining unit 310 may determine the output pattern so that an imaging range specified by the imaging conditions is included.

Also, the multiple elements 201 comprises the sub-coil 210 for each predetermined number, the output pattern determining unit 310 may include the synthetic pattern table having the imaging range 322 for the respective sub-coils 210; the synthetic pattern candidates 325 that the elements 201 comprising the sub-coil 210 can obtain; and the output channel number 326 formed for a candidate of the sub-coil 210 in the respective synthetic patterns, the using element determining unit 311 that determines the using elements 201 in a unit of the sub-coil 210 according to an imaging range in the imaging conditions and determines the sub-coil 210 including the using elements 201 as the using sub-coil 210, and the synthetic pattern determining unit 312 that determines the synthetic pattern for the respective using sub-coils 210 so that the total number of the output channels of the respective using sub-coils 210 is the maximum value equal to or less than the reception channel number.

Also, the synthetic pattern determining unit 312 may determine the synthetic pattern candidate 325 where the using sub-coil 210 closer to the imaging center specified by the imaging conditions has the larger number of output channels as a synthetic pattern.

Also, the synthetic pattern table 320 further has position information of the respective elements 201 comprising the sub-coil 210 for the respective synthetic pattern candidates 325, the synthetic pattern determining unit 312 may determine the synthetic pattern candidate 325 whose synthesization of the reception signals from the elements 201 closer to the imaging center is the least as a synthetic pattern of the respective using sub-coil 210 using the position information according to the imaging conditions.

Also, there may be one arrangement direction of the using elements 201 synthesizing the reception signals.

Also, in a magnetic resonance imaging apparatus of the present embodiment comprising: a reception coil including a plurality of sub-coils comprised of one or more elements; one or more reception channels equal to or less than the number of the elements; a synthesizer synthesizing reception signals received by the respective elements according to the predetermined output pattern and forming the reception channels; a synthetic pattern table having the number of output channels that the sub-coils form using an imaging range for each sub-coil, a synthetic pattern candidate of the reception signals that can be obtained by the elements comprising the sub-coils, and the respective synthetic pattern candidates, the output pattern determining method includes: a using sub-coil determining unit determining a sub-coil used for synthesizing the reception signals as a using sub-coil according to an imaging range of the imaging conditions; a synthetic pattern determining unit determining a synthetic pattern from synthetic pattern candidates of the respective using sub-coils so that the total output channel number of the using sub-coil is the maximum value equal to or less than the number of the reception channels; and an output pattern determining unit determining the output pattern from the using sub-coil and the synthetic pattern.

That is, according to the present embodiment, similarly to the first embodiment, only the reception signals of the elements 201 corresponding to an imaging range are synthesized and output to the signal processing device 230. At this time, the elements 201 receiving signals of a region closer to the attention region in an imaging range are not synthesized and are sent to the signal processing device 230 alone. Therefore, the closer the region is to the attention region, the more the image quality is improved.

Therefore, in the present embodiment, the optimal elements 201 are automatically determined according to a position of an imaging range and the attention region, and a synthetic pattern of reception signals among the elements 201 that use a reception channel maximally is automatically determined. Therefore, reception signals minimally required each time imaging is performed in the synthesizer 220 to generate an image of an imaging range are synthesized in a mode where a reception channel is utilized maximally, and this can be used for image reconstruction and image synthesization. Therefore, according to the present embodiment, high-quality images with a good S/N ratio can be obtained without a burden on a user. Also, similarly to the first embodiment, configurations of the elements 201 can be changed flexibly.

Third Embodiment

Next, the third embodiment applying the present invention will be described. In the present embodiment, restrictions by an imaging range are not set, and the elements 201 closer to the attention region of the imaging range avoids synthesizing the reception signals and becomes a single output signal. That is, the present embodiment prioritizes S/N ratio improvement when an output pattern is determined.

The configuration of the MRI apparatus 100 of the present embodiment is basically similar to the first embodiment. However, the process of the output pattern determining unit 310 varies because items to be prioritized when an output pattern is determined vary. Hereinafter, focusing on different configurations from the first embodiment, the present embodiment will be described. Also, even in the present embodiment, similarly to the first embodiment, a pattern to synthesize reception signals output from the elements 201 is determined on the predetermined sub-coil 210 basis.

The output pattern determining unit 310 of the present embodiment includes the synthetic pattern table 320 and determines an output pattern so that an S/N ratio of a synthesized image obtained by synthesizing images reconstructed from the respective signals after synthesization by the synthesizer 220 is the best. The synthetic pattern table 320 has the configuration similar to the first embodiment.

The output pattern determining unit 310 of the present embodiment selects the synthetic pattern candidate 325 whose S/N ratio is the largest respectively until the total output channel number is the maximum value equal to or less than the reception channel number in order from the sub-coil 210 closer to the imaging center specified by imaging conditions. Here, the synthetic pattern candidate 325 whose S/N ratio is the largest is, for example, a synthetic pattern candidate 325 of which the synthesizing number 324 is the smallest or of which the output channel number 326 is the largest. Then, for the sub-coil 210 next closer to the imaging center, the one having a difference between the total output channel number of the selected sub-coil 210 is selected and the reception channel number for the output channel number 326. Then, the sub-coil 210 selecting the synthetic pattern candidate 325 becomes the using sub-coil 210, and the selected synthetic pattern candidate 325 becomes the synthetic pattern.

Also, the method to define a distance from the imaging center of the respective sub-coils 210 is similar to the second embodiment.

Figure 12:
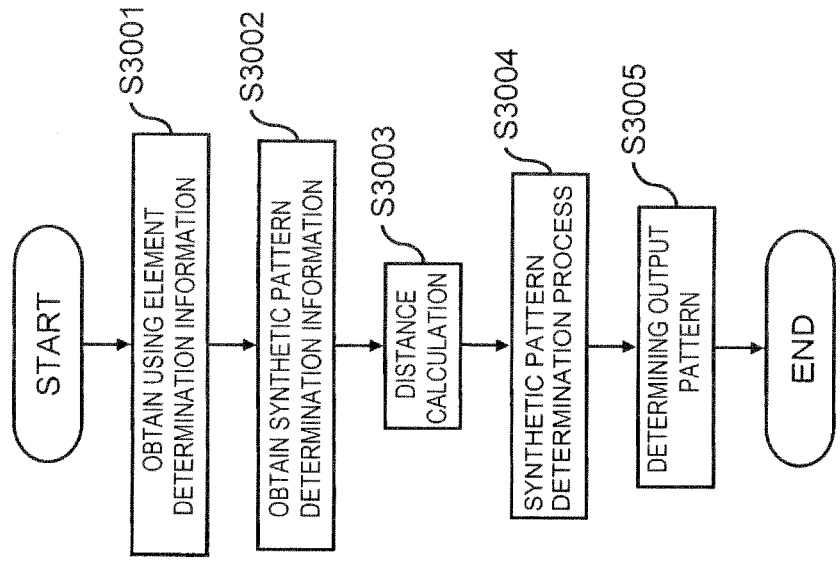
FIG. 12 is a flow chart for determining an output pattern of the third embodiment.

Next, the flow for an output pattern determining process by the output pattern determining unit 310 of the present embodiment will be described. FIG. 12 shows a process flow for the output pattern determining process of the present embodiment. Also, the output pattern determining unit 310 of the present embodiment starts the process immediately after a user completes the settings for imaging conditions and receives a command to start imaging.

The output pattern determining unit 310 obtains information to determine the using sub-coil 210 and the using elements 201 (Step S3001). Here, information related to an imaging range is obtained from imaging conditions, and the position information 322 of the respective sub-coils 210 is obtained from the synthetic pattern table 320. Additionally, in the present embodiment, the position information 322 is used for determining a synthetic pattern.

Next, the output pattern determining unit 310 obtains information to determine a synthetic pattern (Step S3002). Here, the reception number of the signal processing device 230 is obtained. The reception channel number of the signal processing device 230 is stored as device information in the storage device 172 in advance. Either Step S3001 or Step S3002 may be performed first.

Next, the output pattern determining unit 310 calculates a distance from the imaging center of the respective sub-coils 210 using the similar method to the second embodiment (Step S3003). Then, a synthetic pattern determining process to determine the using sub-coil 210 (the using elements 201) and a synthetic pattern of the using sub-coil 210 is performed (Step S3004). The synthetic pattern determining process will be described later. Then, an output pattern is determined (Step S3005) using information of the using sub-coil 210 and a synthetic pattern to finish the process.

Figure 13:
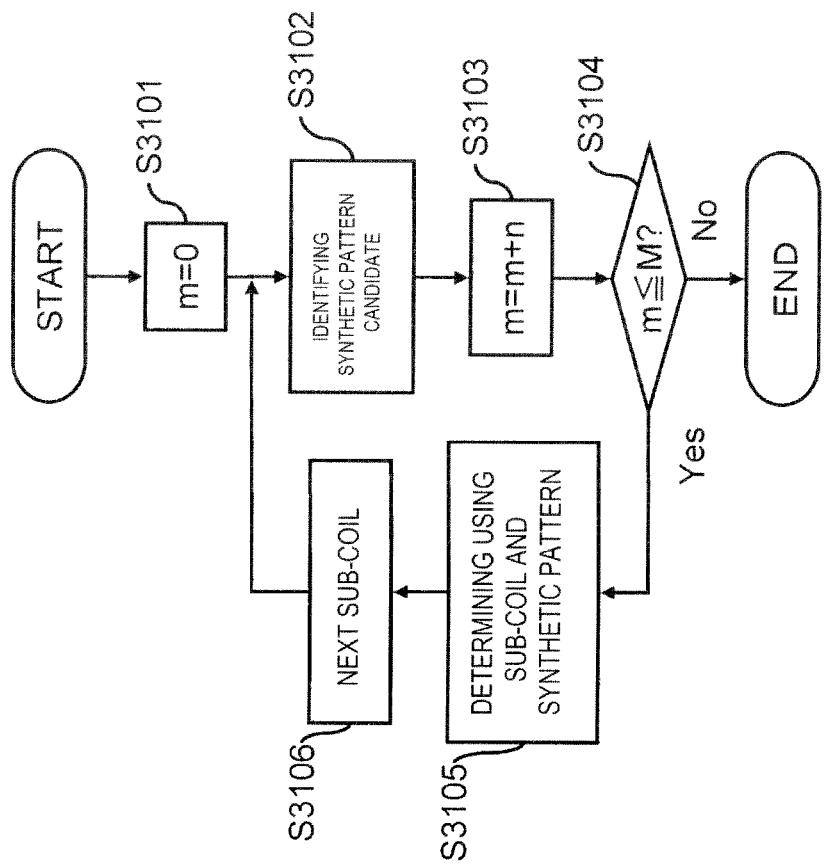
FIG. 13 is a flow chart for determining a synthetic pattern of the third embodiment.

Next, the flow for a synthetic pattern determining process by the output pattern determining unit 310 in the above Step S3004 will be described. FIG. 13 shows the process flow for a synthetic pattern determining process of the present embodiment.

First, the output channel counter m is initialized (m=0) (Step S3101) Then, the synthetic pattern table 320 is referred in order from the sub-coil 210 with a shorter distance to the imaging center to identify a synthetic pattern candidate 325 with the maximum output channel number 326 (Step S3102). Then, the output channel number n of the identified synthetic pattern candidate 325 is added to the output channel counter m (Step S3103). Then, the output channel counter m is compared with the reception channel M (Step S3104).

Here, if the output channel counter m is equal to or less than the reception channel number M, the sub-coil 210 identified the synthetic pattern candidate 325 is determined as the using sub-coil 210, and additionally, the identified synthetic pattern candidate 325 is determined as a synthetic pattern of the using sub-coil 210 (Step S3105). Then, for the next sub-coil 210 (Step S3106), the processes from Step S3102 are repeated.

On the other hand, if the output channel counter m exceeds the reception channel number M in Step S3104, the process is finished.

Figure 14:
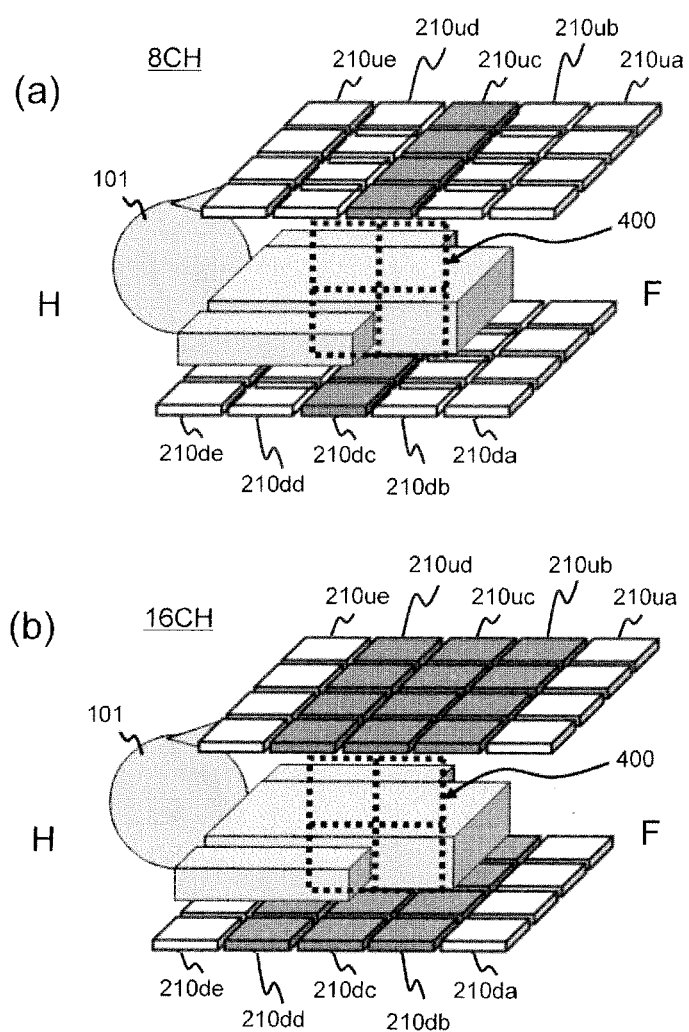
FIGS. 14(a) and (b) are explanatory diagrams to describe the synthetic pattern determination process of the third embodiment.

FIG. 14 is a diagram to describe a specific example of the synthetic pattern determining process of the present embodiment by the output pattern determining unit 310. Additionally, the configuration of the reception coil 161 is similar to that of the reception coil 161 shown in FIG. 6(a) of the first embodiment. Also, the imaging center in the orthogonal direction is the center of the sub-coils 210uc and 210dc. Also, the upper sub-coil group is closer to the imaging center in the order of the sub-coils 210ub, 210ud, 210ua, and 210ue. The lower sub-coil group is also similarly closer to the imaging center in the order of the sub-coils 210db, 210dd, 210da, and 210de.

When the reception channel number of the signal processing device 230 is 8, a synthetic pattern of the subcoils 210uc and 210dc that are closest to the imaging center is determined. Here, referring to the synthetic pattern table 320 shown in FIG. 4, the synthetic pattern candidate A with the maximum output channel number is selected. In this case, the output channel numbers of the synthetic pattern candidate A selected for the subcoils 210uc and 210dc are both 4. Adding these numbers, the total output channels number is 8. In this state, the total output channels number is equal to or less than the reception channel number, therefore, the selected sub-coils 210uc and 210dc are determined as the using sub-coils 210, and additionally, the synthetic pattern candidate A of these using sub-coils 210 is determined as a synthetic pattern.

For the next close sub-coils 210ub and 210db, the synthetic pattern candidate A is similarly identified as the synthetic pattern candidate 325, and the output channel number is added. Then, the total output channels number becomes 16 and exceeds the reception channel number 8. For this reason, the sub-coils 210ub and 210db are not determined as the using sub-coils 210, resulting in finishing the process. Consequently, in this case, as shown in FIG. 14(a), only the sub-coils 210 uc and 210 dc are determined as the using sub-coils 210, and additionally, the respective synthetic patterns are determined as the synthetic pattern candidate A.

Also, when the reception channel number of the signal processing device 230 is 16, a synthetic pattern of the subcoils 210uc and 210dc that are closest to the imaging center is determined. Here, referring to the synthetic pattern table 320 shown in FIG. 4, the synthetic pattern candidate A with the maximum output channel number is selected. In this case, the output channel numbers of the synthetic pattern candidate A selected for the subcoils 210uc and 210dc are both 4. Adding these numbers, the total output channels number is 8. In this state, the total output channels number is equal to or less than the reception channel number, therefore, the selected sub-coils 210uc and 210dc are determined as the using sub-coils 210, and additionally, synthetic patterns of these using sub-coils 210 are determined as the synthetic pattern candidate A.

For the next close sub-coils 210ub and 210db, the synthetic pattern candidate A is similarly identified, and the total output channel number is added. Then, the total output channels number becomes 16.

In this state, the total output channels number is equal to or less than the reception channel number, therefore, the selected sub-coils 210*ub* and 210*db* are determined as the using sub-coils 210, and additionally, synthetic patterns of these using sub-coils 210 are determined as the synthetic pattern candidate A.

For the next close sub-coils 210*ud* and 210*dd*, the synthetic pattern candidate A is similarly identified, and the output channel number is added. Then, the total output channels number becomes 24 and exceeds the reception channel number 16. For this reason, the sub-coils 210*ud* and 210*dd* are not determined as the using sub-coils 210, resulting in finishing the process. Consequently, in this case, as shown in FIG. 14(*b*), only the sub-coils 210*uc*, 210*ub*, 210*dc* and 210*db* are determined as the using sub-coils 210, and additionally, the respective synthetic patterns are determined as the synthetic pattern candidate A.

Also, in the present embodiment, a synthetic pattern in which the output channel number is not the maximum may be selected for the one or more using sub-coils 210 farthest from the imaging center among the using sub-coils 210. In this case, the output pattern determining unit 310 refers to the synthetic pattern table 320 to select a synthetic pattern candidate 325 having a maximum output channel number from among the output channel number 326 in a selectable range for the using sub-coils 210. If there are a plurality of such synthetic pattern candidates 325, a synthetic pattern candidate 325 of which the synthesizing number 324 is the smallest from among the candidates is selected.

Also, even in the present embodiment, similarly to the second embodiment, the configuration may be made so that a different synthetic pattern candidate 325 is registered using a same synthesizing number 324 in the synthetic pattern table. Even in this case, only for the one or more using sub-coils 210 that are the farthest, a synthetic pattern candidate 325 where the elements 201 farther from the imaging center in a synthetic direction is synthesized is selected from among the synthetic pattern candidates 325 having a maximum output channel number 326 from among output channel numbers in a selectable range and the smallest synthesizing number 324.

As described above, a magnetic resonance imaging apparatus of the present embodiment includes the reception coil 161 having a plurality of the elements 201, the synthesizer 220 that synthesizes one or more reception channels equal to or less than the number of the elements 201 and reception signals received by the respective elements 201 according to a predetermined output pattern into an output channel equal to or less than the number of the reception channels to output to the reception channels, and the output pattern determining unit 310 determines a synthetic pattern where information identifying the using elements 201 that are the one or more elements 201 using the reception signals to form the output channel according to imaging conditions and the reception signals among the using elements as an output pattern.

Also, the output pattern determining unit 312 may determine the output pattern so that a signal-noise ratio of a synthetic image obtained by synthesizing images reconstructed from signals for the respective reception channels is the best.

Also, the elements 201 comprise the sub-coil 210 for each predetermined number, the output pattern determining unit 312 includes: an imaging range for the respective sub-coils 210; the synthetic pattern candidates 325 that can be obtained by the elements 201 comprising the sub-coil 210; and the synthetic pattern table 320 that stores the output channel numbers 326 formed of reception signals by the sub-coil 210 in the respective synthetic pattern candidates 325, and the synthetic pattern candidate 325 in which the output channel number 326 is the maximum is respectively selected until the accumulated total of the output channel number 326 reaches a maximum value equal to or less than the reception channel number in order from the sub-coil 210 closer to the imaging center specified by the imaging conditions, and the sub-coil 210 that selects the synthetic pattern candidate 325 as well as the synthetic pattern candidate 325 are determined as the using sub-coil 210 and a synthetic pattern respectively.

Also, there may be one arrangement direction of the using elements 201 synthesizing the reception signals.

Also, in the magnetic resonance imaging apparatus 100 of the present embodiment comprising: the reception coil 161 including a plurality of the sub-coils 210 comprising of the one or more elements 201; the one or more reception channels the synthesizer 220 forming the reception channels by synthesizing the one or more reception channels equal to or less than the number of the elements 201 and reception signals received by the respective elements 201 according to the predetermined output pattern; an imaging range for the respective sub-coils 210; the synthetic pattern candidates 325 of the reception signals that can be obtained by the elements 201 comprising the sub-coil 210; and the synthetic pattern table 320 storing the output channel numbers formed by the sub-coil 210 for the respective synthetic pattern candidates 325, the output pattern determining method may includes a synthetic pattern determining unit determines the sub-coil 210 that selected the synthetic pattern candidate 325 and the synthetic pattern candidate 325 as the using sub-coil 210 and a synthetic pattern respectively by selecting the synthetic pattern candidate 325 with the maximum output channel number 326 respectively in order from the sub-coil 210 closer to the imaging center specified by the imaging conditions until the accumulated total of the output channel numbers 326 becomes a maximum value equal to or less than the reception channel number and an output pattern determining unit determining the output pattern from the using sub-coil 210 and the synthetic pattern.

That is, according to the present embodiment, reception signals of the elements 201 that receive signals from a region closer to an attention region in the synthesizer 220 are determined as reception signals preferentially. Then, the spare reception channels and the reception signals of the remaining elements are effectively synthesized into output signals. Therefore, according to the present embodiment, image quality around the attention region can be enhanced without a burden on a user.

Additionally, similarly to the first and second embodiments, configurations of the elements 201 can be changed flexibly.

Fourth Embodiment

Next, the fourth embodiment applying to the present invention will be described. In the present embodiment, synthetic directions among the elements 201 are not limited to one direction such as back-and-forth, left-and-right, and top-and-bottom. Also, when a synthetic pattern is determined, imaging conditions are considered.

The configuration of the MRI apparatus 100 of the present embodiment is basically similar to that of the first embodiment. Also, even in the present embodiment, similarly to the first embodiment, a pattern to synthesize reception signals output from the elements 201 is determined in a unit of the predetermined sub-coil 201. However, in the present embodiment, because synthetic directions in the sub-coil 210 are not limited to one direction, arrangement configuration of the elements 201 comprising the sub-coil 210 does not matter. There should be two or more elements 201 included in the sub-coil 210. For example, the sub-coil 210 may have all the elements 201.

Figure 15:
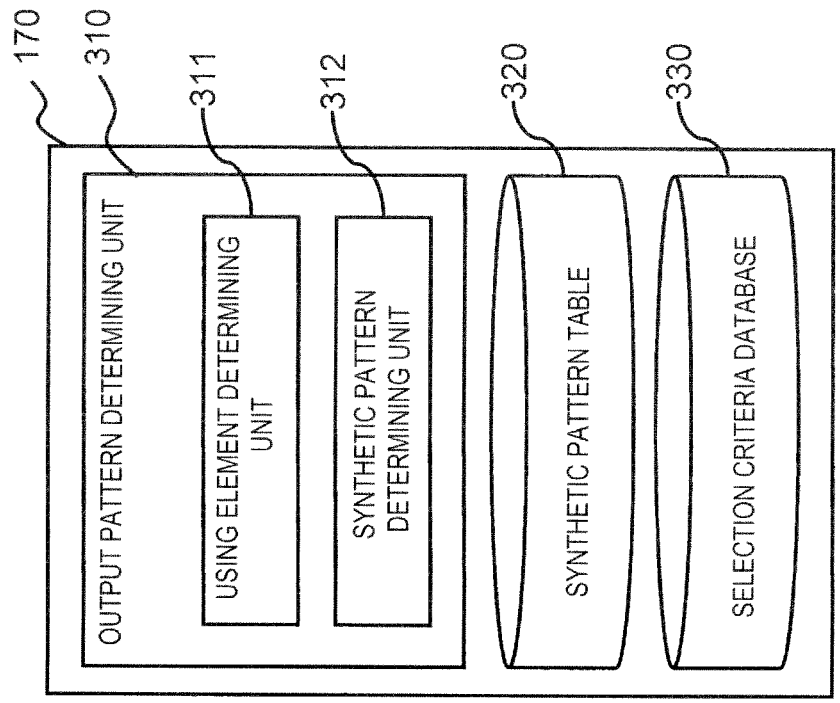
FIG. 15 is a functional block diagram of a control system of the forth embodiment.

Also, in the present embodiment, because synthetic directions are not limited to one direction, information to be registered as the synthetic pattern table 320 in advance varies. Also, when a synthetic pattern is selected, processes of the synthetic pattern determining unit 312 vary as imaging conditions are considered. Additionally, when a synthetic pattern is determined, as shown in FIG. 15, the control system 170 of the present embodiment includes the selection criteria database 330 that specifies synthetic pattern selection criteria for each imaging condition in addition to the configuration of the first embodiment because imaging conditions are considered. Hereinafter, focusing on different configurations from the first embodiment, the present embodiment will be described.

Figure 16:
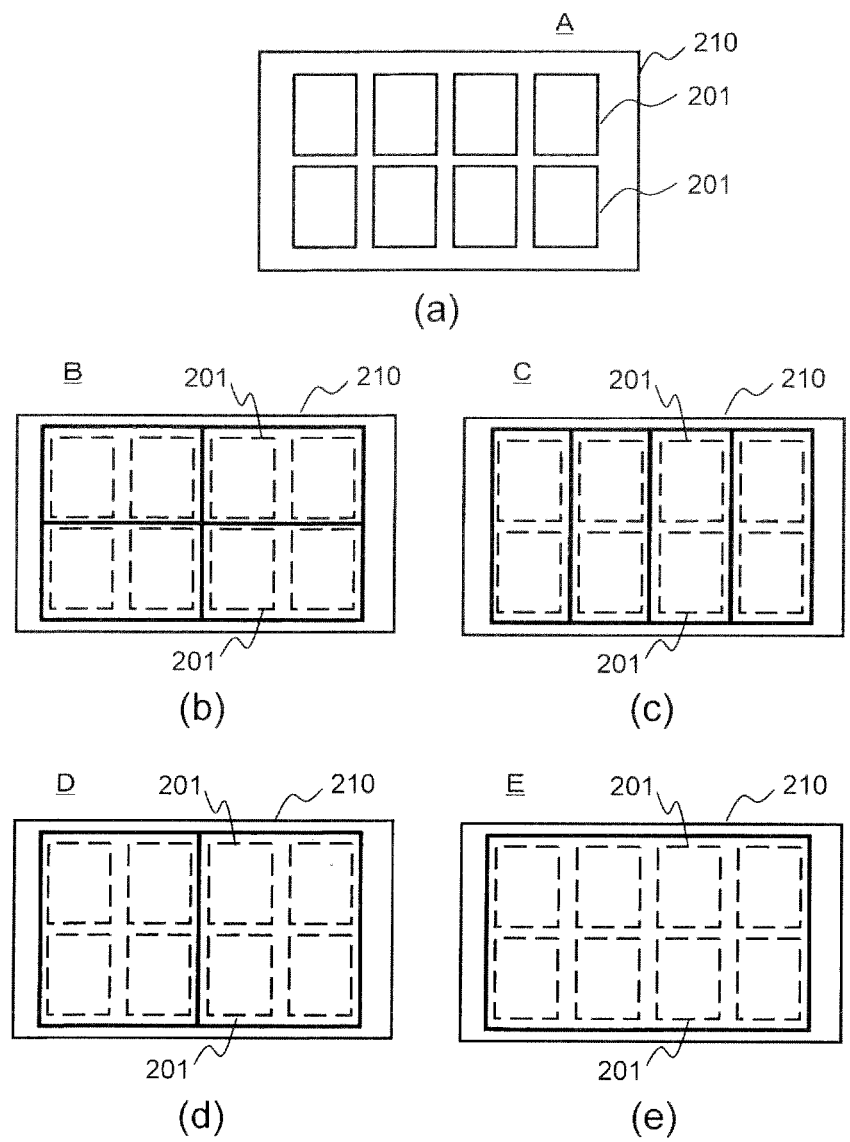
FIG. 16 is an explanatory diagram to describe examples for synthetic pattern candidates of the forth embodiment.

First, a synthetic pattern (synthetic pattern candidate) that can be obtained by the sub-coil 210 of the present embodiment will be described. FIG. 16 is a diagram to describe an example of a synthetic pattern candidate of the sub-coil 210 of the present embodiment. Here, as an example, a case where one sub-coil 210 is comprised of the total eight elements 201 of four elements in the horizontal (row) direction and two elements in the vertical (column) direction is shown.

In such sub-coil 210, for example, the five types of the synthetic pattern candidates 325 shown in FIGS. 16(a) to (e) are registered in the synthetic pattern table 320. The synthetic pattern candidate A shown in FIG. 16(a) is, so to speak, a synthetic pattern candidate 325 that is non-synthesized and does not synthesize any reception signals. The synthetic pattern candidate B shown in FIG. 16(b) is a synthetic pattern candidate 325 with the synthesizing number: 2 and the output channel number: 4 that synthesizes reception signals of the two horizontally adjacent elements 201. The synthetic pattern candidate C shown in FIG. 16(c) is a synthetic pattern candidate 325 with the synthesizing number: 2 and the output channel number: 4 that synthesizes reception signals of the two vertically adjacent elements 201. The synthetic pattern candidate D shown in FIG. 16(d) is a synthetic pattern candidate 325 with the synthesizing number: 4 and the output channel number: 2 that synthesizes reception signals of the four vertically and horizontally adjacent elements 201. The synthetic pattern candidate E shown in FIG. 16(e) is a synthetic pattern candidate 325 with the synthesizing number: 8 and the output channel number: 1 that synthesizes reception signals of all the elements 201 comprising the sub-coil 210. Also, synthetic pattern candidates of the present embodiment are not limited to the above candidates.

An example of the synthetic pattern table 320 of the present embodiment in which such synthetic pattern candidates are registered will be described. FIG. 17 is an example of the synthetic pattern table 320 of the present embodiment. Similarly to the first embodiment, the sub-coil name 321, the position information 322, the synthetic pattern candidate name 323, the synthesizing number 324, the synthetic pattern candidate 325, and the channel (output channel) number 326 that is output after synthesization using the synthetic pattern for the respective sub-coils 210 are registered also in the synthetic pattern table 320 of the present embodiment.

Because synthesization can be performed in multiple directions in the present embodiment, however, a plurality of the synthetic pattern candidates 325 can be registered for a case where the synthesizing number 324 is 1 differently from the first embodiment. Also, in addition to the total synthesizing numbers 324, the synthesizing numbers 324 in the respective synthesizing directions are registered for the synthesizing numbers 324. Here, as an example, a case where the synthesizing numbers 324 in the row and column directions are registered is shown. Obviously, in a case where synthesization in the vertical direction is also performed, the synthesizing numbers 324 in the vertical direction may be registered.

Also, because imaging conditions are considered when the synthetic pattern determining unit 312 determines a synthetic pattern, the synthetic pattern candidate 325, similarly to the second embodiment, includes element layout information that can comprehend layout information of the respective elements 201 synthesizing the reception signals.

Here, as an example, a case where the sub-coil 210 of #001 is comprised of the four elements 201 disposed in row and a case where the sub-coil 210 of #002 is comprised of the eight elements 201 of four columns and two rows are shown. The synthetic pattern candidates 325 to be registered are not limited to the above cases.

Also, the using element determining unit 311 of the present embodiment, similarly to the first embodiment, the smallest sub-coil 210 that covers an imaging range specified by imaging conditions set by a user is identified based on the position information 322 of the synthetic pattern table 320 and determined as the sub-coil to be used (using sub-coil) 210. Then, the elements 201 included in the using sub-coil 210 is determined as the using elements 201.

In the selection criteria database 330, criteria to select a synthetic pattern are registered for each imaging condition. Here, associating with imaging conditions, selection criteria with the greatest efficiency among the elements are registered.

For example, in the case of parallel imaging, an NMR signal is measured while thinning out phase encode steps in a measuring space using a plurality of the elements to shorten a measuring time. At this time, in order to remove artifacts, matrix calculation is performed using sensitivity distribution of the respective elements. Therefore, the less the synthesizing number in a parallel imaging direction is, the higher the image quality can be produced. Therefore, associating with parallel imaging, information such as selecting a less synthesizing number in the parallel imaging direction is registered. Also, the selection criteria database 330 is created in advance and registered in the storage device 172.

Next, a synthetic pattern determining process by the synthetic pattern determining unit 312 of the present embodiment will be described. The synthetic pattern determining unit 312 of the present embodiment, similarly to the first embodiment, the synthesizing numbers 324 of the respective sub-coils 210 are the same. Then, within a range where the total of the output channel numbers 326 does not exceed the reception channel M, the synthetic pattern candidate 325 having the smallest synthesizing number 324 is determined as a synthetic pattern of the respective using sub-coils 210. At this time, if there are a plurality of the synthetic pattern candidates 325 for the determined synthesizing number 324, selection is performed according to selection criteria registered in the selection criteria database 330.

For example, if the reception channel number M is 8 in a case where the two sub-coils 210 of #001 and #002 shown in FIG. 17 is the using sub-coil 210, the total of the output channel number becomes 12 when the synthesizing number is 1 and exceeds the reception channel number M. Next, when the synthesizing number is 2, the total of the output channel number becomes 6 even if either of the synthetic pattern candidate B or the synthetic pattern candidate C is adopted for #002 and is smaller than the reception channel number M. Therefore, a synthetic pattern candidate of the synthesizing number 2 is determined as a synthetic pattern for both the using sub-coils 210.

At this time, as described above, there are the synthetic pattern B and the synthetic pattern C for synthetic pattern candidates where the synthesizing number 324 of the elements 201 of #002 is 2. For example, in the case of parallel imaging, information such as selecting a synthetic pattern with the smallest synthesizing number in the parallel imaging direction is registered as selection criteria. For example, if the parallel imaging direction specified by imaging conditions is a column direction (vertical direction), the synthetic pattern candidate B with the smallest synthesizing number 324 in a column direction is selected from among synthetic pattern candidates where the synthesizing number 324 is 2 and is determined as a synthetic pattern.

As described above, a magnetic resonance imaging apparatus of the present embodiment includes the reception coil 161 having a plurality of the elements 201, one or more reception channels equal to or less than the number of the elements 201, the synthesizer 220 synthesizing reception signals received by the respective elements 201 into an output channel equal to or less than the number of the reception channel according to the predetermined output pattern and outputting to the reception channel, and the output pattern determining unit 310 determining information that identifies the using elements 201 which are the one or more elements 201 to use the reception signals for forming the output channel according to imaging conditions and a synthetic pattern for synthesizing the reception signals among the using elements 201 as an output pattern.

Also, the output pattern determining unit 310 may determine the output pattern so that an imaging range specified by the imaging conditions is included.

Also, the elements 201 comprise the sub-coil 210 for each predetermined number, and the output pattern determining unit 310 may include the synthetic pattern table 320 having the imaging range 322 for the respective sub-coils 210; the synthetic pattern candidates 325 that can be obtained by the elements 201 comprising the sub-coil 210; and the output channel numbers 326 formed in the candidate sub-coil 210 for each synthetic pattern, the using element determining unit 311 determining the using elements 201 in a unit of the using sub-coil 210 according to an imaging range in the imaging conditions and determining the sub-coil 210 that includes the elements 201 as the using sub-coil 210, and the synthetic pattern determining unit 312 determining the synthetic pattern for the respective using sub-coils 210 so that the total of the output channel numbers by the respective using sub-coils 210 becomes a maximum value equal to or less than the reception channel number.

Also, the synthetic pattern table 320 further has the synthesizing number 324 that is a maximum number of reception signals synthesized with the synthetic pattern candidate 325 for the respective synthetic pattern candidates 325, and the synthetic pattern determining unit 312 may determine the synthetic pattern candidate 325 of which the synthesizing number 324 is the same for the respective using sub-coils 210 as a synthetic pattern.

Also, as a synthetic pattern, the synthetic pattern determining unit 312 may determine the synthetic pattern candidate 325 where the using sub-coil 210 closer to the imaging center specified by the imaging conditions has more output channel numbers.

Also, the synthetic pattern table 320 further includes layout information of the respective elements 201 comprising the sub-coil 210 for the respective synthetic pattern candidates 325, and the synthetic pattern determining unit 312, using the layout information, may determine the synthetic pattern candidate 325 that has the smallest synthesizing number of reception signals from the elements 201 closer to the imaging center according to the imaging conditions as a synthetic pattern of the respective using sub-coils 210.

Also, the using elements that synthesize the reception signals may be arranged in two or more directions.

Also, in a case where imaging identified by the imaging conditions is parallel imaging, the output pattern determining unit may determine the synthetic pattern so that a synthesizing number in a parallel imaging direction specified by the imaging conditions is the smallest.

Also, in a magnetic resonance imaging apparatus of the present embodiment comprising: a reception coil including a plurality of sub-coils that are comprised of one or more elements; one or more reception channels that are equal to or less than the number of the elements; a synthesizer synthesizing reception signals received by the respective elements into the reception channels according to a predetermined output pattern; and a synthetic pattern table including an imaging range for the respective sub-coils, synthetic pattern candidates of the reception signals that can be obtained by the elements comprising the sub-coils, and the number of output channels that the sub-coils form for the respective synthetic pattern candidates, the output pattern determining method may include: a using sub-coil determining unit determining a sub-coil to be used for synthesizing the reception signals as a using sub-coil according to an imaging range of the imaging conditions; a synthetic pattern determining unit determining a synthetic pattern from synthetic pattern candidates of the respective using sub-coils so that the total output channel number of the using sub-coil is a maximum value equal to or less than the reception channel number; and an output pattern determining unit determining the output pattern from the using sub-coil and the synthetic pattern.

Therefore, similarly to the first embodiment, the present embodiment automatically determines the optimal elements 201 according to an imaging range and also automatically determines a synthetic pattern of reception signals among the elements 201 that use reception channels maximally. Therefore, reception signals that are minimally required to generate an image in an imaging range in the synthesizer 220 each time imaging is performed are synthesized in a mode where the reception channel is maximally utilized and can be used for image reconstruction and image synthesization. For this reason, according to the present embodiment, high quality images with a good S/N ratio can be obtained without a burden on a user. Also, increasing and decreasing the elements 201 can be performed flexibly using a simple process such as changing a synthetic pattern table.

Also, in the present embodiment, an optimal synthetic pattern can be selected according to the imaging type, and measuring can be more efficient according to the imaging.

Also, in the present embodiment, the process of the synthetic pattern determining unit 312 is described based on that of the synthetic pattern determining unit 312 of the first embodiment, but the process is not limited to the above. For example, similarly to the second embodiment, the number of output channels may be determined according to the distance from the imaging center.

Also, similarly to the third embodiment, it may be configured so that the output pattern determining unit 310 determines the using elements 201 with an S/N ratio prioritized without the using element determining unit 311 and the synthetic pattern determining unit 312. That is, the sub-coils 210, in order from those closer to the imaging center to those where the total number of output channels of the synthetic pattern candidates 325 with a maximum S/N ratio does not exceed the number of reception channels, are determined as the using sub-coils 210, and the respective synthetic patterns becomes the synthetic pattern candidate 325 whose S/N ratio is maximum.

Also, it may be configured so that the control system 170 can perform any processes from the first embodiment to the third embodiment and can automatically select which method is used to determine an output pattern.

In this case, the control system 170 further includes a determination method selection unit and a method selection criteria database. In this case, which output pattern determining method to use for each imaging condition among the first embodiment, the second embodiment, and the third embodiment is registered in the method selection criteria database as selection criteria in advance. The determination method selection unit determines an output pattern using a registered method associated with imaging conditions set by a user.

Additionally, even in the fourth embodiment, similarly, it may be configured so that any one of the processes based on the output pattern determining methods of the respective embodiments is feasible and selectable.

Also, in the above respective embodiments, it is described that the control system 170 included in the MRI apparatus 100 achieves the output pattern determining unit 310 and the synthetic pattern table 320, however, this is not limited to the above. They may be constructed on an information processing device that can communicate data with the MRI apparatus 100 and is independent from the MRI apparatus 100.

DESCRIPTION OF REFERENCE NUMERALS

100: MRI apparatus, 101: object, 120: static magnetic field generating system, 130: gradient magnetic field generating system, 131: gradient magnetic field coil, 132: gradient magnetic field power source, 140: sequencer, 150: transmission system, 151: transmission coil, 152: transmission processing unit, 160: reception system, 161: reception coil, 162: reception processing unit, 170: control system, 171: CPU, 172: storage device, 173: display device, 174: input device, 201: element, 210: sub-coil, 210*da*: sub-coil, 210*db*: sub-coil, 210*dc*: sub-coil, 210*dd*: sub-coil, 210*de*: sub-coil, 210*ua*: sub-coil, 210*ub*: sub-coil, 210*uc*: sub-coil, 210*ud*: sub-coil, 210*ue*: sub-coil, 220: synthesizer, 230: signal processing device, 310: output pattern determining unit, 311: using element determining unit, 312: synthetic pattern determining unit, 320: synthetic pattern table, 321: sub-coil name, 322: position information, 323: synthetic pattern candidate name, 324: synthesizing number, 325: synthetic pattern candidate, 326: output channel number, 330: selection criteria database, 400: imaging range, 500: output pattern

The invention claimed is:

1. A magnetic resonance imaging apparatus, comprising:
   a reception coil including a plurality of sub-coils and a plurality of elements;
   one or more reception channels;
   an output pattern determining unit to determine (a) information that identifies using elements used for forming an output channel and from among the plurality of elements and (b) a synthetic pattern for synthesizing reception signals received by the using elements as an output pattern and according to imaging conditions so that a number of the output channels to be formed is equal to or less than a number of the reception channels; and
   a synthesizer to synthesize reception signals received by the using elements according to the output pattern to form the output channels and to output the synthesized reception signals to the reception channels,
   wherein the output pattern determining unit includes a synthetic pattern table that registers, for each sub-coil amongst the sub-coils, an imaging range for the sub-coil, at least one synthetic pattern candidate that can be obtained by a corresponding number of elements constituting the sub-coil, and a number of output channels that are formed by reception signals received through the sub-coil, for each synthetic pattern candidate amongst the at least one synthetic pattern candidate, and
   the output pattern determining unit determines the output pattern so as to maximize a S/N ratio of a synthesized image synthesized based on images reconstructed from the signals received through the reception channels, and wherein
   the output pattern determining unit considers each sub-coil in turn in order from a sub-coil closer to an imaging center specified by the imaging conditions, to select a synthetic pattern candidate in which the number of the output channels is the maximum is selected until an accumulated total number of the output channels reaches a maximum value equal to or less than a number of the reception channels, and
   the output pattern and the using sub-coil are determined based on the selected synthetic pattern candidate and the sub-coil registered in association with the selected synthetic pattern candidate in the synthetic pattern table.

2. The magnetic resonance imaging apparatus according to claim 1,
   wherein the output pattern determining unit determines the output pattern so as to include the imaging range specified by the imaging conditions.

3. The magnetic resonance imaging apparatus according to claim 1, wherein
   the synthetic pattern table further holds a synthesizing number that is a maximum number of reception signals synthesized in the synthetic pattern candidates for each of the synthetic pattern candidates, and
   the synthetic pattern determining unit determines a synthetic pattern candidate where the synthesizing number is the same for each of the using sub-coils as the synthetic pattern.

4. The magnetic resonance imaging apparatus according to claim 1, wherein the synthetic pattern determining unit determines a synthetic pattern candidate where a using sub-coil closer to an imaging center specified by the imaging conditions having the largest number of output channels.

5. The magnetic resonance imaging apparatus according to claim 1, wherein
   the synthetic pattern candidate in which the number of the output channels is the maximum is respectively selected until an accumulated total number of the output channels reaches the maximum value equal to or less than the number of the reception channel number channels in order from a sub-coil closer to an imaging center specified by the imaging conditions, and a sub-coil that selects the synthetic pattern candidate as well as the synthetic pattern candidate are determined as the using sub-coil and the synthetic pattern respectively.

6. The magnetic resonance imaging apparatus according to claim 4, wherein
the synthetic pattern table further includes layout information of the respective elements comprising the sub-coil for each synthetic pattern candidate, and
the synthetic pattern determining unit determines a synthetic pattern candidate in which the synthesizing number of reception signals from elements closer to the imaging center is the least as a synthetic pattern of each of the using sub-coils according to the imaging conditions using the layout information.

7. The magnetic resonance imaging apparatus according to claim 1, wherein the using elements that synthesize the reception signals are arranged in one direction.

8. The magnetic resonance imaging apparatus according to claim 1, wherein the using elements that synthesize the reception signals are arranged in two or more directions.

9. The magnetic resonance imaging apparatus according to claim 8, wherein
the output pattern determining unit determines the synthetic pattern so that a synthesizing number in a parallel imaging direction specified by the imaging conditions is the smallest in a case where imaging identified by the imaging conditions is parallel imaging.

10. The magnetic resonance imaging apparatus according to claim 1, wherein the plurality of elements are disposed in a position where the elements face each other across an object.

11. The magnetic resonance imaging apparatus according to claim 1, further comprising:
a display unit to display the imaging conditions,
wherein the output pattern determining unit displays the determined output pattern on the display.

12. An output pattern determining method performed by a magnetic resonance imaging apparatus comprising:
a reception coil including a plurality of sub-coils each having one or more elements;
one or more reception channels;
a synthesizer to synthesize reception signals received by the elements according to a selected output pattern that corresponds to the reception channels; and
a synthetic pattern table that registers, for each sub-coil amongst the sub-coils, an imaging range for the sub-coil, at least one synthetic pattern candidate that can be obtained by a corresponding number of elements constituting the sub-coil, and a number of output channels that are formed by reception signals received through the sub-coil, for each synthetic pattern candidate amongst the at least one synthetic pattern candidate,
the output pattern determining method comprising:
determining a sub-coil to be used as a using sub-coil for synthesizing the reception signals according to an imaging range of the imaging conditions;
determining a synthetic pattern from synthetic pattern candidates of the using sub-coil so that a number of the output channels corresponding to the using sub-coil reaches a maximum value equal to or less than a number of the reception channels; and
determining the output pattern so as to maximize a S/N ratio of a synthesized image synthesized based on images reconstructed from the signals received through the reception channels, and considering each sub-coil in turn in order from a sub-coil closer to an imaging center specified by the imaging conditions, to select a synthetic pattern candidate in which the number of the output channels is the maximum is selected until an accumulated total number of the output channels reaches a maximum value equal to or less than a number of the reception channels,
the output pattern and the using sub-coil being determined based on the selected synthetic pattern candidate and the sub-coil registered in association with the selected synthetic pattern candidate in the synthetic pattern table.

* * * * *